(12) United States Patent
Sandmore et al.

(10) Patent No.: US 9,220,436 B2
(45) Date of Patent: Dec. 29, 2015

(54) TECHNIQUE FOR REMANUFACTURING A BIS SENSOR

(75) Inventors: Donald R. Sandmore, Lyons, CO (US); David P. Besko, Thornton, CO (US)

(73) Assignee: Covidien LP, Mansfield, MA (US)

( * ) Notice: Subject to any disclaimer, the term of this patent is extended or adjusted under 35 U.S.C. 154(b) by 741 days.

(21) Appl. No.: 13/245,040

(22) Filed: Sep. 26, 2011

(65) Prior Publication Data

US 2013/0079618 A1  Mar. 28, 2013

(51) Int. Cl.
*A61B 5/0478* (2006.01)
*A61B 5/00* (2006.01)

(52) U.S. Cl.
CPC ............. *A61B 5/0478* (2013.01); *A61B 5/6839* (2013.01); *A61B 5/6814* (2013.01); *A61B 2560/0475* (2013.01); *A61B 2562/0209* (2013.01); *A61B 2562/125* (2013.01); *Y10T 29/4973* (2015.01); *Y10T 29/49732* (2015.01)

(58) Field of Classification Search
CPC .. A61B 5/0006; A61B 5/0478; A61B 5/0464; A61B 5/4821; A61B 5/6803; A61B 5/6814; A61B 5/6832; A61B 2560/0443; A61B 2560/045; A61B 2562/08; A61B 2562/085; A61B 2562/125; A61B 2562/14; A61B 2562/226; A61B 2562/227; A61B 2560/0475
USPC ......... 600/372, 391–393, 396, 554, 382, 383, 600/544, 545; 29/402.01, 825, 592.1
See application file for complete search history.

(56) References Cited

U.S. PATENT DOCUMENTS

| | | | | |
|---|---|---|---|---|
| 4,121,573 A | * | 10/1978 | Crovella et al. | 600/382 |
| 4,353,372 A | * | 10/1982 | Ayer | 600/393 |
| 5,217,013 A | | 6/1993 | Lewis et al. | |

(Continued)

FOREIGN PATENT DOCUMENTS

| | | |
|---|---|---|
| DE | 3516338 | 11/1986 |
| DE | 3703458 | 8/1988 |

(Continued)

OTHER PUBLICATIONS

US Food and Drug Administration, "Reprocessing of Single-Use Devices > Frequently Asked Questions" at http://www.fda.gov/MedicalDevices/DeviceRegulationandGuidance/ReprocessingofSingle-UseDevices/ucm121093.htm (2001), accessed May 2014.*

(Continued)

*Primary Examiner* — Linda Dvorak
*Assistant Examiner* — Erin M Cardinal
(74) *Attorney, Agent, or Firm* — Fletcher Yoder PC

(57) ABSTRACT

Remanufactured BIS sensors and methods for remanufacturing used BIS sensors are provided. Such a remanufactured sensor may include certain components from a used medical sensor and certain new components. For example, a remanufactured BIS sensor may include a backing layer and at least first, second, and third electrodes disposed on the backing layer having a conductive ink. The first, second, and third electrodes are adapted to be in electrical contact with a patient to perform BIS measurements. A foam layer may be disposed on at least a portion of the backing layer, and an adhesive may be attached to the foam layer and is configured to secure the remanufactured BIS sensor to the patient. The first electrode, the second electrode, the third electrode, the backing layer, or a combination thereof, may be new and the foam layer, the adhesive, or a combination thereof, may be from a used medical sensor.

16 Claims, 15 Drawing Sheets

(56) References Cited

U.S. PATENT DOCUMENTS

| | | | |
|---|---|---|---|
| 5,584,296 A | 12/1996 | Cui et al. | |
| 5,772,591 A * | 6/1998 | Cram | 600/383 |
| 5,797,841 A | 8/1998 | Delonzor et al. | |
| 5,830,137 A | 11/1998 | Scharf | |
| 6,032,064 A | 2/2000 | Devlin et al. | |
| 6,032,072 A * | 2/2000 | Greenwald et al. | 600/544 |
| 6,128,521 A * | 10/2000 | Marro et al. | 600/383 |
| 6,171,258 B1 | 1/2001 | Karakasoglu et al. | |
| 6,173,196 B1 | 1/2001 | Delonzor et al. | |
| 6,330,468 B1 | 12/2001 | Scharf | |
| 6,394,953 B1 * | 5/2002 | Devlin et al. | 600/383 |
| 6,430,423 B2 | 8/2002 | Delonzor et al. | |
| 6,434,410 B1 * | 8/2002 | Cordero et al. | 600/396 |
| 6,654,626 B2 | 11/2003 | Devlin et al. | |
| 6,728,564 B2 | 4/2004 | Lahteenmaki | |
| 6,763,255 B2 | 7/2004 | Delonzor et al. | |
| 6,934,570 B2 | 8/2005 | Kiani et al. | |
| 6,934,571 B2 | 8/2005 | Wiesmann et al. | |
| 7,047,056 B2 | 5/2006 | Hannula et al. | |
| 7,048,687 B1 | 5/2006 | Reuss et al. | |
| 7,130,673 B2 * | 10/2006 | Tolvanen-Laakso et al. | 600/383 |
| 7,164,938 B2 | 1/2007 | Geddes et al. | |
| 7,190,984 B1 | 3/2007 | Delonzor et al. | |
| 7,206,630 B1 * | 4/2007 | Tarler | 600/509 |
| 7,215,994 B2 * | 5/2007 | Huiku | 600/544 |
| 7,248,910 B2 | 7/2007 | Li et al. | |
| 7,257,438 B2 | 8/2007 | Kinast | |
| 7,289,837 B2 | 10/2007 | Mannheimer et al. | |
| 7,297,119 B2 | 11/2007 | Westbrook et al. | |
| 7,321,790 B2 | 1/2008 | Delonzor et al. | |
| 7,369,886 B2 | 5/2008 | Delonzor et al. | |
| 7,373,188 B2 | 5/2008 | Delonzor et al. | |
| 7,373,189 B2 | 5/2008 | Delonzor et al. | |
| 7,373,190 B2 | 5/2008 | Delonzor et al. | |
| 7,373,191 B2 | 5/2008 | Delonzor et al. | |
| 7,386,334 B2 | 6/2008 | Delonzor et al. | |
| 7,389,130 B2 | 6/2008 | Delonzor et al. | |
| 7,418,284 B2 | 8/2008 | Delonzor et al. | |
| 7,486,979 B2 * | 2/2009 | Matlock | 600/344 |
| 8,116,841 B2 * | 2/2012 | Bly et al. | 600/391 |
| 2002/0019588 A1 | 2/2002 | Marro et al. | |
| 2003/0009096 A1 * | 1/2003 | Lahteenmaki | 600/383 |
| 2003/0130585 A1 * | 7/2003 | Wenger | 600/509 |
| 2003/0225323 A1 | 12/2003 | Kiani et al. | |
| 2004/0117891 A1 | 6/2004 | Hannula et al. | |
| 2004/0260161 A1 | 12/2004 | Melker et al. | |
| 2004/0267104 A1 | 12/2004 | Hannula et al. | |
| 2005/0059869 A1 | 3/2005 | Scharf et al. | |
| 2005/0070776 A1 | 3/2005 | Mannheimer et al. | |
| 2005/0131288 A1 * | 6/2005 | Turner et al. | 600/391 |
| 2005/0277819 A1 | 12/2005 | Kiani et al. | |
| 2005/0283082 A1 | 12/2005 | Geddes et al. | |
| 2006/0064024 A1 | 3/2006 | Schnall | |
| 2006/0161054 A1 | 7/2006 | Reuss et al. | |
| 2006/0195028 A1 | 8/2006 | Hannula et al. | |
| 2006/0258930 A1 * | 11/2006 | Wu et al. | 600/383 |
| 2006/0264722 A1 | 11/2006 | Hannula et al. | |
| 2006/0264723 A1 | 11/2006 | Hannula et al. | |
| 2006/0264724 A1 | 11/2006 | Hannula et al. | |
| 2006/0264725 A1 | 11/2006 | Hannula et al. | |
| 2006/0264727 A1 | 11/2006 | Mannheimer et al. | |
| 2006/0281984 A1 | 12/2006 | Mannheimer et al. | |
| 2007/0021659 A1 | 1/2007 | Delonzor et al. | |
| 2007/0021660 A1 | 1/2007 | Delonzor et al. | |
| 2007/0021662 A1 | 1/2007 | Delonzor et al. | |
| 2007/0027378 A1 | 2/2007 | Delonzor et al. | |
| 2007/0027379 A1 | 2/2007 | Delonzor et al. | |
| 2007/0027380 A1 | 2/2007 | Delonzar et al. | |
| 2007/0142715 A1 | 6/2007 | Banet et al. | |
| 2007/0208269 A1 | 9/2007 | Mumford et al. | |
| 2008/0081971 A1 | 4/2008 | Ollerdessen | |
| 2008/0088467 A1 | 4/2008 | Al-Ali | |
| 2008/0154111 A1 | 6/2008 | Wu et al. | |
| 2008/0221413 A1 | 9/2008 | Hoarau | |
| 2008/0228053 A1 | 9/2008 | Wang et al. | |
| 2008/0316488 A1 | 12/2008 | Mao et al. | |
| 2009/0105577 A1 | 4/2009 | Wu et al. | |
| 2009/0209840 A1 * | 8/2009 | Axelgaard | 600/391 |
| 2009/0323267 A1 | 12/2009 | Besko et al. | |
| 2010/0041962 A1 * | 2/2010 | Causevic et al. | 600/301 |
| 2010/0076282 A1 | 3/2010 | Sandmore | |
| 2010/0081902 A1 | 4/2010 | McKenna et al. | |
| 2010/0249554 A1 | 9/2010 | McKenna et al. | |
| 2010/0249557 A1 | 9/2010 | Besko et al. | |
| 2010/0331638 A1 | 12/2010 | Besko et al. | |
| 2011/0190600 A1 * | 8/2011 | McKenna et al. | 600/301 |
| 2012/0071742 A1 | 3/2012 | Medina et al. | |
| 2012/0131233 A1 * | 5/2012 | Rantala | 710/12 |
| 2012/0216335 A1 | 8/2012 | McKenna et al. | |
| 2012/0253148 A1 | 10/2012 | Haisley et al. | |
| 2012/0253152 A1 | 10/2012 | Haisley et al. | |
| 2012/0253159 A1 | 10/2012 | Medina et al. | |
| 2012/0253163 A1 * | 10/2012 | Afanasewicz et al. | 600/383 |

FOREIGN PATENT DOCUMENTS

| | | |
|---|---|---|
| DE | 19632361 | 2/1997 |
| EP | 0127947 | 12/1984 |
| EP | 0204259 | 12/1986 |
| EP | 0531631 | 3/1993 |
| FR | 2685865 | 7/1993 |
| JP | 6014906 | 1/1994 |
| JP | 2004148069 | 5/2004 |
| JP | 2006122458 | 5/2006 |
| JP | 2006201114 | 8/2006 |
| JP | 2006239267 | 9/2006 |
| WO | WO9502358 | 1/1995 |
| WO | WO9736536 | 10/1997 |
| WO | WO 0059374 A1 * | 10/2000 |

OTHER PUBLICATIONS

Soto, Denise A.; "A Comparative Study of Pulse Oximeter Measurements: Digit Versus Earlobe," Master of Science Thesis, California State University Dominguez Hills, May 1997, 46 pgs.

Faisst, Karin, et al.; "Intrapartum Reflectance Pulse Oximetry: Effects of Sensor Location and Fixation Duration on Oxygen Saturation Readings," *Journal of Clinical Monitoring*, vol. 13, pp. 299-302 (1997).

Izumi, Akio, et al.; "Accuracy and Utility of a New Reflectance Pulse Oximeter for Fetal Monitoring During Labor," *Journal of Clinical Monitoring*, vol. 13, pp. 103-108 (1997).

"Smaller Product, Tighter Tolerances Pose Dispensing Challenges for Medical Device Manufacturer," *Adhesives Age*, pp. 40-41 (Oct. 1997).

Hall, J.D., et al.; "Bispectral index: comparison of two montages", *British Journal of Anaesthesia* 1998; 80: 342-344.

DeKock, Marc; "Pulse Oximetry Probe Adhesive Disks: a Potential for Infant Aspiration," *Anesthesiology*, vol. 89, pp. 1603-1604 (1998).

Rohling, Roman, et al.; "Clinical Investigation of a New Combined Pulse Oximetry and Carbon Dioxide Tension Sensor in Adult Anaesthesia," *Journal of Clinical Monitoring and Computing*, vol. 15; pp. 23-27 (1999).

Schulz, Christian Eric; "Design of a Pulse Oximetry Sensor Housing Assembly," California State University Master's Thesis, *UMI Dissertation Services*, UMI No. 1401306, (May 2000) 63 pages.

Yokota, Nakaura, Takahashi, et al.; "Pilot Model of a Reflectance-Type Pulse Oximeter for Pre-hospital Evaluation," *Journal of the Japanese Society of Emergency Medicine*, Kanto Region, vol. 21, pp. 26-27 (2000) (Article in Japanese—contains English summary.

Cubeddu, Rinaldo, et al.; "Portable 8-channel time-resolved optical imager for functional studies of biological tissues," *Photon Migration, Optical Coherence Tomography, and Microscopy, Proceedings of SPIE*, vol. 4431, pp. 260-265 (2001).

Gisiger, P.A., et al.; "OxiCarbo®, a single sensor for the non-invasive measurement of arterial oxygen saturation and $CO_2$ partial pressure at the ear lobe," *Sensor and Actuators*, vol. B-76, pp. 527-530 (2001).

Gosney, S., et al.; "An alternative position for the pulse oximeter probe," *Anaesthesia*, vol. 56, p. 493 (2001).

(56) References Cited

OTHER PUBLICATIONS

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Kyriacou, Panayiotis A., et al.; "Esophageal Pulse Oximetry Utilizing Reflectance Photoplethysmography," *IEEE Transactions on Biomedical Engineering*, vol. 49, No. 11, pp. 1360-1368 (Nov. 2002).

Kyriacou, P. A., et al.; "Investigation of esophageal photoplethysmographic signals and blood oxygen saturation measurements in cardiothoracic surgery patients," *Physiological Measurement*, vol. 23, No. 3, pp. 533-545 (Aug. 2002).

Irie, A., et al.; "Respiration Monitors—Pulse Oximeters," *Neonatal Care*, vol. 15, No. 12, pp. 78-83 (2002) (Article in Japanese—contains English summary of article).

Shaltis, Phillip, et al.; "Implementation and Validation of a Power-Efficient, High-Speed Modulation Design for Wireless Oxygen Saturation Measurement Systems," *IEEE*, pp. 193-194 (2002).

Warren, Steve, et al.; "Wearable Sensors and Component-Based Design for Home Health Care," *Proceedings of the Second Joint EMBS/BMES Conference*, Houston, Texas; Oct. 23-26, 2002; pp. 1871-1872.

Manberg, Paul J., Ph.D..; Letters to the Editor "BIS Monitoring Requires Proper Electrode Placement for Optimum Performance", *Anesth Anag* 2003; 97:1206.

Matsui, A., et al.; "Pulse Oximeter," *Neonatal Care*, vol. 16, No. 3, pp. 38-45 (2003) (Article in Japanese—contains English summary of article).

Nakagawa, M., et al.; "Oxygen Saturation Monitor," *Neonatal Monitoring*, vol. 26, No. 5, pp. 536-539 (2003) (Article in Japanese—contains English summary of article).

Bentley, David J. et al.; "Measure Pressure with Thin Film"; Paper Film & Foil Converter; May 1, 2003.

Mannheimer, Paul D., et al.; "The influence of Larger Subcutaneous Blood Vessels on Pulse Oximetry," *Journal of clinical Monitoring and Computing*, vol. 18, pp. 179-188 (2004).

Wendelken, Suzanne, et al.; "The Feasibility of Using a Forehead Reflectance Pulse Oximeter for Automated Remote Triage," *IEEE*, pp. 180-181 (2004).

Sugino, Shigekzau, et al.; "Forehead is as sensitive as finger pulse oximetry during general anesthesia," *Can J. Anesth.; General Anesthesia*, vol. 51, No. 5; pp. 432-436 (2004).

Kocher, Serge, et al.; "Performance of a Digital $PCO_2/SPO_2$ Ear Sensor," *Journal of Clinical Monitoring and Computing*, vol. 18, pp. 75-59 (2004).

Johnston, William S., et al.; "Effects of Motion Artifacts on helmet-Mounted Pulse Oximeter Sensors," 2 pgs. (2004).

Branche, Paul C., et al.; "Measurement Reproducibility and Sensor Placement Considerations in Designing a Wearable Pulse Oximeter for Military Applications," 2 pgs. (2004).

Shiraishi, Toshie, et al.; "A Comparison of Frontal and Occipital Bispectral Index Values Obtained During Neurosurgical Proceduresm", *Anesth Analg.* 2004; 98:1773-5.

Author Unknown; "Aspect Medical Systems Operating Manual", copyright 2006, 102 pages.

Dahaba, Ashraf A., et al.; "BIS-VistaTM Occipital Montage in Patients Undergoing Neurosurgical Procedures during Propofol-Remifentanil Anesthesia", *Anesthesiology*, 2010: 112645-51.

Author Unknown; "BIS-VistaTM Monitoring System Bilateral Monitoring Addendum", Aspect Medical Systems, Inc., copyright 2010, 22 pages.

"BIS Integrated Solutions"; Phillips, Inc. (2006), 2 pages.

"Aspect Medical Systems Continuum of Care"; Anandic Medical Systems (2006), 17 pages.

\* cited by examiner

TECHNIQUE FOR REMANUFACTURING A BIS SENSOR

BACKGROUND

The present disclosure relates generally to remanufactured medical devices and, more particularly, to remanufacturing sensors used for sensing physiological parameters of a patient.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring certain physiological characteristics of a patient. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as electroencephalography (EEG), and the devices built based upon electroencephalographic techniques are commonly referred to as EEG monitors. EEG monitors use non-invasive electrophysiological monitoring to evaluate global changes in a patient's condition, for example, during surgical procedures. Examples of global changes may include assessing the effects of anesthetics, evaluating asymmetric activity between the left and right hemispheres of the brain in order to detect cerebral ischemia, and detecting burst suppression. One such technique includes bispectral index (BIS) monitoring to measure the level of consciousness by algorithmic analysis of a patient's EEG during general anesthesia.

EEG measurements are captured using EEG monitoring devices, and sensors associated with these monitoring devices are applied to the patient. Typically, the sensors include electrodes that may be applied to various anatomies of the patient (e.g., the temple and/or forehead). For example, sensors for BIS monitoring may include a single strip that includes several electrodes for placement on the forehead to noninvasively acquire an EEG signal. Because the BIS sensors are placed in direct contact with a patient, and possibly patient fluids, BIS sensors are typically intended for use with a single patient. Thus, BIS sensors are typically discarded after use.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
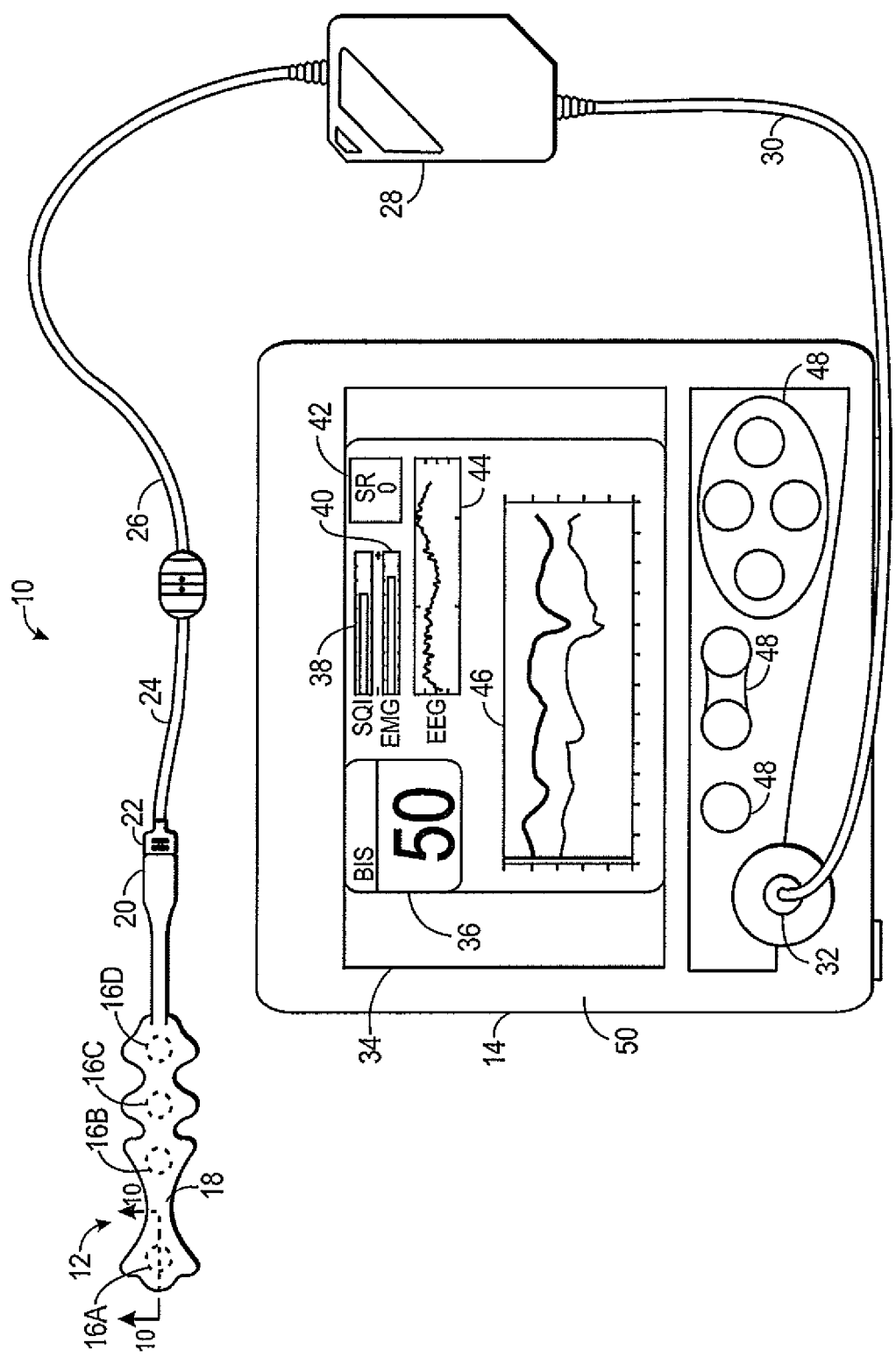
FIG. 1 is a front view of an embodiment of a monitoring system configured to be used with a sensor for performing BIS measurements, in accordance with an aspect of the present disclosure.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The present disclosure is generally directed to the remanufacturing of bispectral index (BIS) sensors having one or more electrodes for monitoring brain activity of a patient. For example, the sensors described herein may include one or more electrodes, such as at least two electrodes, for capturing electrical data from a patient's brain, and features for facilitating the capture and transmittal of the data from the patient to a patient monitor. Thus, the BIS sensors described herein may be constructed using a combination of new materials (i.e., materials that have not been incorporated into a BIS sensor) and components taken from one or more used BIS sensors (e.g., an electrode). For example, a BIS sensor may include a base layer supporting a flexible array of electrodes configured to capture electrical data from a patient, a conductive gel to facilitate the transmission of the electrical signals from the patient to the sensor, one or more foam pieces to pad the BIS sensor, and an adhesive layer for attaching the sensor to the patient, such as to the patient's forehead and/or temple. Accordingly, BIS sensors constructed using the remanufacturing techniques described herein may incorporate used foam layers, flexible circuits, and, in certain embodiments, existing but unused adhesive layers, or any combination thereof.

By way of example, a BIS™ sensor available from Aspect Medical Systems, Inc., such as a BIS™ Quattro sensor, a BIS™ extend sensor, a BIS™ pediatric sensor, or a BIS™ bilateral sensor, which include a plurality of printed electrodes on a flexible substrate, represent one type of EEG sensor. It should be noted, however, that the present disclosure is applicable to any EEG or similar sensor having similar or the same materials and/or configuration as those described herein. Further, other sensors having some or all of the components described herein (e.g., ECG sensors, general EEG sensors, pulse oximetry sensors, or sensors used for measuring water fraction or hematocrit) may benefit from the disclosed techniques. The BIS sensors disclosed herein may be used in conjunction with any suitable monitoring system, which is described with respect to FIG. 1. An example BIS sensor and its components are discussed with respect to FIG. 2, and a packaged EEG sensor is discussed with respect to FIG. 3. As noted above, these sensors are generally known to be one-time-use sensors that may be discarded after use by one patient. Though disposable, some components of these used sensors, such as the conductors, connectors, and memory units associated therewith, may be employed in the construction of remanufactured sensors. Reusing these components to reconstruct a sensor may reduce waste (e.g., plastic waste materials), consequently reducing an impact on the environment, while accordingly reducing costs. Various embodiments of remanufacturing techniques and the configurations that result are discussed with respect to FIGS. 4-33.

With the foregoing in mind, FIG. 1 is a front view of an embodiment of a patient monitoring system 10. The monitoring system 10 may include a sensor 12 and an EEG monitor 14. The sensor 12 may include electrodes 16 (e.g., four electrodes 16A, 16B, 16C, and 16D) that may be self adherent and self prepping to temple and forehead areas of a patient and that are used to acquire EEG signals. As discussed in detail below, the electrodes 16 may include a printed conductive ink supported within a flexible sensor body 18 to provide enhanced flexibility and conformance to patient tissue. The sensor 12 may include a paddle connector 20, which couples through a connector 22 to a cable 24 (e.g., a patient interface cable), which in turn may be coupled to a cable 26 (e.g., a pigtail cable). In certain embodiments, the sensor 12 may be coupled to the cable 26 thereby eliminating the cable 24. The cable 26 may be coupled to a digital signal converter 28, which in turn is coupled to the cable 30 (e.g., a monitor interface cable). In certain embodiments, the digital signal converter 28 may be embedded in the monitor 14 to eliminate the cables 26 and 30. Cable 26 may be coupled to the monitor 14 via a port 32 (e.g., a digital signal converter port).

The monitor 14 may be capable of calculating physiological characteristics relating to the EEG signal received from the sensor 12. For example, the monitor may be capable of algorithmically calculating BIS from the EEG signal. BIS is a measure of a patient's level of consciousness during general anesthesia. Further, the monitor 14 may include a display 34 capable of displaying physiological characteristics, historical trends of physiological characteristics, other information about the system (e.g., instructions for placement of the sensor 12 on the patient), and/or alarm indications. The monitor 14 may display a patient's BIS value 36. The BIS value 36 represents a dimensionless number (e.g., ranging from 0, i.e., silence, to 100, i.e., fully awake and alert) output from a multivariate discriminate analysis that quantifies the overall bispectral properties (e.g., frequency, power, and phase) of the EEG signal. For example, a BIS value 36 between 40 and 60 may indicate an appropriate level for general anesthesia. The monitor 14 may also display a signal quality index (SQI) bar graph 38 (e.g., ranging from 0 to 100) which measures the signal quality of the EEG channel source(s) based on impedance data, artifacts, and other variables. The monitor 14 may yet also display an electromyograph (EMG) bar graph 40 (e.g., ranging from 30 to 55 decibels) which indicates the power (e.g., in decibels) in the frequency range of 70 to 110 Hz. The frequency range may include power from muscle activity and other high-frequency artifacts. The monitor 14 may further display a suppression ratio (SR) 42 (e.g., ranging from 0 to 100 percent), which represents the percentage of epochs over a given time period (e.g., the past 63 seconds) in which the EEG signal is considered suppressed (i.e., low activity). In certain embodiments, the monitor 14 may also display a burst count for the number of EEG bursts per minute, where a "burst" is defined as a short period of EEG activity preceded and followed by periods of inactivity or suppression. The monitor 14 may yet further display the EEG waveform 44. In certain embodiments, the EEG waveform 42 may be filtered. The monitor 14 may still further display trends 46 over a certain time period (e.g., one hour) for EEG, SR, EMG, SQL and/or other parameters. In certain embodiments, the monitor 14 may display stepwise instructions for placing the sensor 12 on the patient. In addition, the monitor 14 may display a verification screen verifying the proper placement of each electrode 16 of the sensor 12 on the patient. In certain embodiments, the monitor 14 may store instructions on a memory specific to a specific sensor type or model, which is discussed in further detail below. In other embodiments, the sensor 12 may include a memory that provides the instructions to the monitor 14.

Additionally, the monitor 14 may include various activation mechanisms 48 (e.g., buttons and switches) to facilitate management and operation of the monitor 14. For example, the monitor 14 may include function keys (e.g., keys with varying functions), a power switch, adjustment buttons, an alarm silence button, and so forth. It should be noted that in other embodiments, the parameters described above and the activation mechanisms 48 may be arranged on different parts of the monitor 14. In other words, the parameters and activation mechanisms 48 need not be located on a front panel 50 of the monitor 14. Indeed, in some embodiments, activation mechanisms 48 are virtual representations in a display or actual components disposed on separate devices. In addition, the activation mechanisms 48 may allow selecting or inputting of a specific sensor type or model in order to access instructions stored within the memory of the sensor 12.

Figure 2:
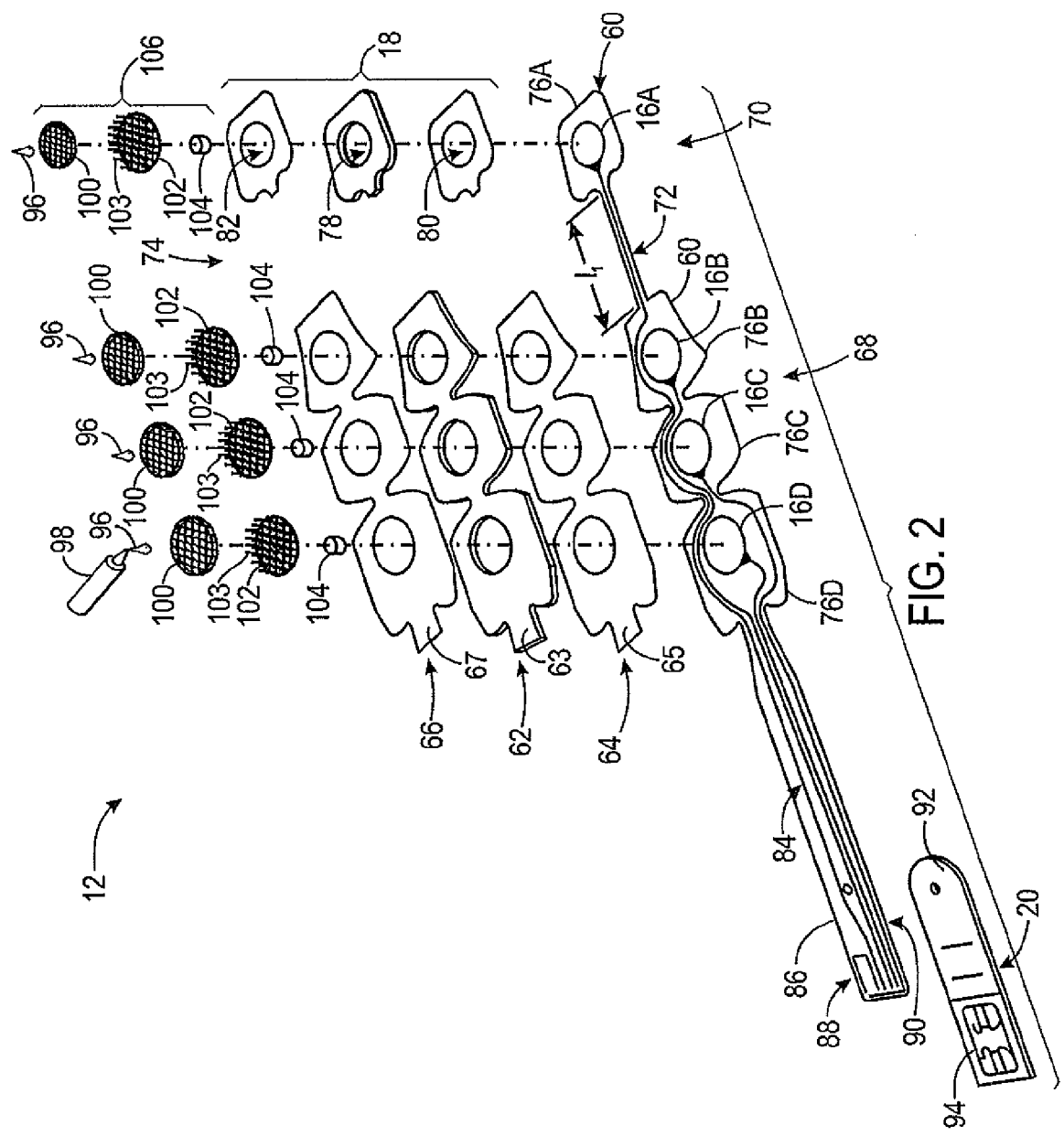
FIG. 2 is an exploded perspective view of an embodiment of the sensor of FIG. 1, in accordance with an aspect of the present disclosure.

One embodiment of the various components of the sensor 12 is illustrated with respect to FIG. 2, which may generally represent the BIS™ Quattro sensor, the BIS™ extend sensor, the BIS™ pediatric sensor, or the BIS™ bilateral sensor mentioned above. For example, the embodiment of the sensor 12 illustrated in FIG. 2 may represent a BIS™ Quattro sensor, wherein electrode 16A is configured to function as a sensing electrode, electrode 16B is configured to monitor artifacts resulting from muscular movement, such as eye twitching, electrode 16C is configured to function as a grounding electrode, and electrode 16D is configured to function as a reference electrode. It should be noted that in certain embodiments, the sensor 12 may be capable of performing BIS measurements with fewer than four electrodes 16, or more than four electrodes 16. For example, in one embodiment, the sensor 12 may be capable of performing BIS measurements using only electrodes 16A, 16C, and 16D. In other embodiments, such as where the sensor 12 is a BIS™ bilateral sensor, the electrodes 16 may include a reference electrode configured to be placed at the center of the patient's forehead, two electrodes each configured to be placed above an eye of the patient to monitor artifacts from eye twitching or movement, one ground electrode, and two electrodes each configured to be placed against the patient's temples for monitoring.

As illustrated, the sensor 12 includes a base structural layer 60, a foam layer 62, a first adhesive 64 configured to secure the foam layer 62 to the base structural layer 60, and a patient-contacting adhesive 66 configured to secure the sensor 12 to a patient. The base structural layer 60 may be constructed from any flexible polymeric material suitable for use in medical devices, such as polyester, polyurethane, polypropylene, polyethylene, polyvinylchloride, acrylics, nitrile, PVC films, acetates, or similar materials that facilitate conformance of the sensor 12 to the patient. On the other hand, the foam layer 62 may be relatively rigid compared to the base structural layer 60 to provide padding and additional comfort to the patient. As an example, the foam layer 62 may include any foam material suitable for use in medical applications, such as polyester foam, polyethylene foam, polyurethane foam, or the like. The first adhesive 64 and the patient-contacting adhesive 66 may include pressure sensitive adhesives such as an acrylic-based adhesive, a supported transfer tape, an unsupported transfer tape, or any combination thereof. In certain embodiments, the patient-contacting adhesive 66 may include a hydrocolloid or similar adhesive for patients with sensitive skin. It should be noted that the foam layer 62 and adhesives 64, 66 may be provided as discrete layers as illustrated, or may be provided as a single piece. That is, the foam layer 62 and the adhesives 64, 66 may be provided as a double-coated foam layer. In embodiments where the adhesives 64, 66 are provided as discrete layers, the foam layer 62 and the adhesives 64, 66 may also include respective tabs 63, 65, 67 to facilitate removal of each layer 62, 64, 66 during remanufacture. Together, the base structural and foam layers 60, 62 and adhesives 64, 66, form the sensor body 18, which is the structural support in which the features for collecting EEG-related data from the patient are disposed.

The sensor body 18 may be configured to facilitate proper placement of the sensor 12 on a patient's head. For example, the sensor body 18 may include a first body portion 68 and a second body portion 70 that are joined by a thin bridge 72 of the base structural layer 60, and are separated by a discontinuation 74 in the foam layer 62 and adhesives 64, 66. Because the base structural layer 60 may be constructed from a flexible polymeric material, the bridge 72 is able to bend with a relatively high degree of freedom (e.g., compared to the foam layer 62). In certain configurations, the electrodes 16B, 16C, and 16D, which are located on the first body portion 68, may be placed on a patient's forehead, while electrode 16A, which is located on the second body portion 70, is placed on the patient's temple. Therefore, because the bridge 72 can easily bend, the sensor 12 is able to accommodate a variety of distances between the forehead and temple areas (i.e., head sizes) by enabling the sensor 12 to arch, twist, or flex between the first and second body portions 68, 70.

It should be noted that the illustrated placement of the bridge 72 is only one embodiment, and that the bridge 72 may be placed between other electrodes 16 in other configurations. For example, in embodiments where the sensor 12 is a BIS™ pediatric sensor or similar sensor, the bridge 72 may be between the electrode 16B and the electrode 16C rather than the illustrated placement. Further, the sensor 12 may include more than one bridge 72, such as two or more bridges 72 disposed between the electrodes 16 (e.g., in a BIS™ bilateral sensor). Furthermore, a length $l_1$ of the bridge 72 may be varied depending on the end use of the sensor 12 (e.g., pediatric, small, regular, or large sizes). Alternatively or additionally, as discussed below, the sensor 12 may not include a bridge portion and may include configurations similar to those described in U.S. patent application Ser. No. 13/074,127 entitled "Method and System for Positioning a Sensor," filed Mar. 28, 2011, which is incorporated by reference herein in its entirety for all purposes.

The base structural layer 60 of the sensor 12 also includes a plurality of electrode portions 76 each having a particular shape. The shape of the electrode portions 76 may be configured to facilitate retention of the sensor 12 on the patient, and, more specifically, to maintain pressure of the corresponding electrode 16 on the electrode portion 76 against the patient's forehead or temple. As illustrated, the electrodes 16 are generally positioned at the center of their respective electrode portion 76. The shapes of the electrode portions 76 may also be reflected in the shape of the foam layer 62 and the adhesives 64, 66, and, more specifically, the portions of the foam layer 62 and the adhesives 64, 66 that may attach to corresponding electrode portions 76 of the base structural layer 60. The foam layer 62 and the adhesives 64, 66 also include respective holes 78, 80, 82 corresponding to the position of the electrodes 16 to facilitate electrical contact with the patient.

As will be appreciated, the electrodes 16 are constructed from conductive materials to enable the sensor 12 to perform electrical measurements on the patient. Specifically, in accordance with certain embodiments, the electrodes 16 are formed from flexible conductive materials, such as one or more conductive inks. For example, the electrodes 16 may be produced by printing (e.g., screen printing or flexographic printing) a conductive ink on the base structural layer 60 and allowing the ink to dry and/or cure. In certain embodiments, the ink may be thermally cured. The sensor 12 may also include a plurality of conductors 84 disposed (e.g., screen or flexographically printed) on the base structural layer 60 to transmit signals to and from each of the electrodes 16 and to enhance flexibility of the sensor 12. The conductors 84 may be formed from the same or a different conductive ink than the electrodes 16. Suitable conductive inks for the electrodes 16 and the conductors 84 may include inks having one or more conductive materials such as metals (e.g., copper (Cu) or silver (Ag)) and/or metal ions (e.g., silver chloride (AgCl)), filler-impregnated polymers (e.g., polymers mixed with conductive fillers such as graphene, conductive nanotubes, metal particles), or any ink having a conductive material capable of providing conductivity at levels suitable for performing the EEG or other electrical measurements. As an example, the electrodes 16 and/or conductors 84 may be formed from an ink having a mixture of Ag and AgCl. Indeed, in certain embodiments, silver and salts thereof (e.g., Ag/AgCl) may be desirable to use for the electrodes 16 and conductors 84 due to its enhanced stability (e.g., compared to copper and copper salts) during certain medical procedures, such as defibrillation. For example, the Ag/AgCl may enable the sensor to depolarize within a desired amount of time (e.g., seconds rather than minutes). This depolarization within a short amount of time may enable the sensor 12 to be used a short time after the defibrillation or similar procedure. However, in a general sense, any suitable conductive material may be used for the electrodes 16 and the conductors 84.

The conductors 84, as noted above, are generally configured to transmit signals to and/or from the electrodes 16. Thus, the conductors 84 may be configured transmit signals such as power, data, and the like, collected at or transmitted to each of the electrodes 16 to or from a tail portion 86 of the base structural layer 60. The tail portion 86 of the base structural layer 60 includes an interface region 88 in which the sensor 12 is configured to couple to another connector or the monitor 14 to enable the monitor 14 to perform BIS measurements. Additionally, the tail portion 86 may be a flat, flexible protrusion from the body portion 18 of the sensor 12 to enable the sensor 12 to be worn by the patient with minimal discomfort by reducing the bulk and weight of the sensor 12 on the patient.

The tail portion 86 and the paddle connector 20 interface with one another at respective overlapping connection regions 90, 92. This enables the sensor 12 to physically couple to the connector 22 or the monitor 14 of FIG. 1. As an example, the paddle connector 20 may be configured to enable the sensor 12 to clip into the connector 22 and/or the monitor 14. The paddle connector 20 may also include a memory unit 94 configured to store information relating to the sensor 12, and to provide the stored information to the monitor 14. For example, the memory unit 94 may store code configured to provide an indication to the monitor 14 as to the make/model of the sensor 12, the time-in-operation of the sensor 12, the number of times the sensor 12 has been remanufactured, or the like. Alternatively or additionally, the memory unit 94 may include code configured to perform a time-out function where the sensor 12 is deactivated after a predetermined number of connections, time-in-operation, or similar use-related metric. In certain embodiments, the memory unit 94 may also store patient-specific and/or sensor-specific information such as trend data collected by the electrodes 16, calibration data related to the electrodes 16 and/or conductors 84, and so on. In other words, the memory unit 94 may be configured to enable the sensor 12 to be used in conjunction with the monitor 14 for the collection of patient data.

As noted, the sensor 12 may be kept in electrical contact with the patient for the collection of EEG or similar data.

Accordingly, the sensor 12 may also include a conductive gel 96 configured to conduct electrical signals between the electrodes 16 and the patient tissue. Generally, the conductive gel 96 may include a wet gel or a hydrogel that is compatible with the materials used for the electrodes 16 and the conductors 84. The conductive gel 96 may include a salt (e.g., sodium chloride (NaCl) or potassium chloride (KCl)) having an ionic concentration suitable for conducting electrical signals between the patient and the electrodes 16. For example, the concentration of chloride ions in the conductive gel 96 may be between approximately 2 and 10% by weight.

The conductive gel 96 may be disposed within electrode wells (e.g., FIG. 10) corresponding to each of the electrodes 16 and defined by the base structural layer 60, the foam layer 62, and the holes 78. As illustrated, the conductive gel 96 may be applied by a tube or packet 98 over the corresponding position of the electrodes 16. However, as discussed below, in some embodiments the conductive gel 96 may be provided as a bubble of gel that is disposed in each electrode well and is configured to burst when applied to the patient. Further, in certain embodiments, the conductive gel 96 may have a viscosity that enables the conductive gel 96 to be self-supporting. In such embodiments, the conductive gel 96 may be the only material disposed within the electrode wells. However, in the illustrated embodiment, the conductive gel 96 may have a viscosity such that the conductive gel 96 may not remain within the electrode wells before the sensor 12 is applied to the patient. Accordingly, the sensor 12 may also include a series of gel support structures 100 that are configured to support the conductive gel 96 in the sensor 12 (i.e., within each electrode well). In accordance with an embodiment, the gel support structures 100 may include an open cell foam sponge material configured to hold the conductive gel 96 within the wells.

Figure 13:
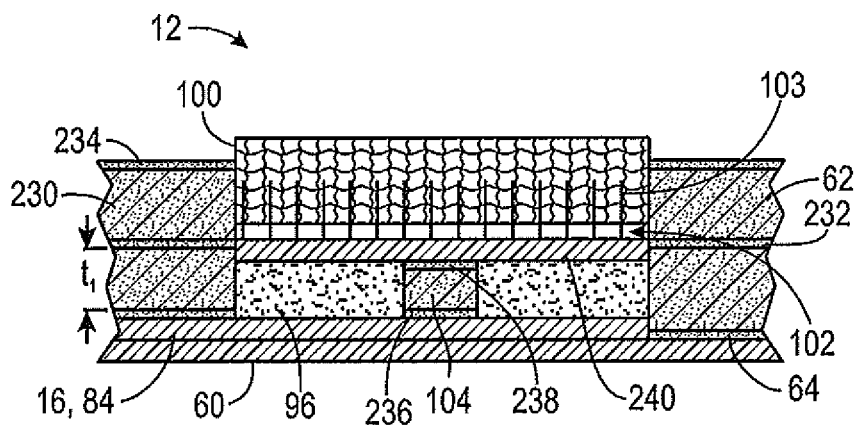
FIG. 13 is a cross-sectional view, taken along line 10-10, of an embodiment of the sensor of FIGS. 1-3 having multiple foam layers, in accordance with an aspect of the present disclosure.

The gel support structures 100 may each be disposed over respective preparation surfaces 102, each of which include a series of protrusions 103. By way of example, the preparation surfaces 102 may include a plastic material, such as a plastic backing and associated set of protrusions produced by modification (e.g., shaving) of a hook portion of a hook and loop fastener. The protrusions 103 of the preparation surfaces 102 may prepare the patient for monitoring by penetrating the interface between the patient's skin and the electrodes 16. Thus, in certain embodiments, the sensor 12 may be considered to be a self-prepping sensor. The preparation surfaces 102 may be secured to the electrodes 16 by adhesive foam dots 104. Collectively, the gel support structures 100, the preparation surfaces 102, and the adhesive foam dots 104 may be referred to as electrode well structures 106. The adhesive foam dots 104, which may be formed from the same or a different foam material than the foam layer 62, attach directly to the electrodes 16. Generally, the adhesive foam dots 104 will have a cylindrical shape, though they may be any suitable shape and size. The adhesive foam dots 104 may have a surface area at each axial extent that is smaller than a surface area of each electrode 16 such that a sufficient portion of the electrodes 16 are left uncovered to ensure suitable conductance between the electrodes 16 and the patient. The adhesive foam dots 104 may be double-coated with adhesive, as illustrated, or may have discrete adhesive layers attached at each axial extent, as illustrated in FIG. 13. In certain embodiments, the gel support structures 100 may be sized so as to be substantially flush with, or stand slightly proud of, the sensor body 18.

The components of the sensor 12 described above may be assembled generally as illustrated in FIG. 2, though other configurations may be possible, as discussed in detail below.

Figure 3:
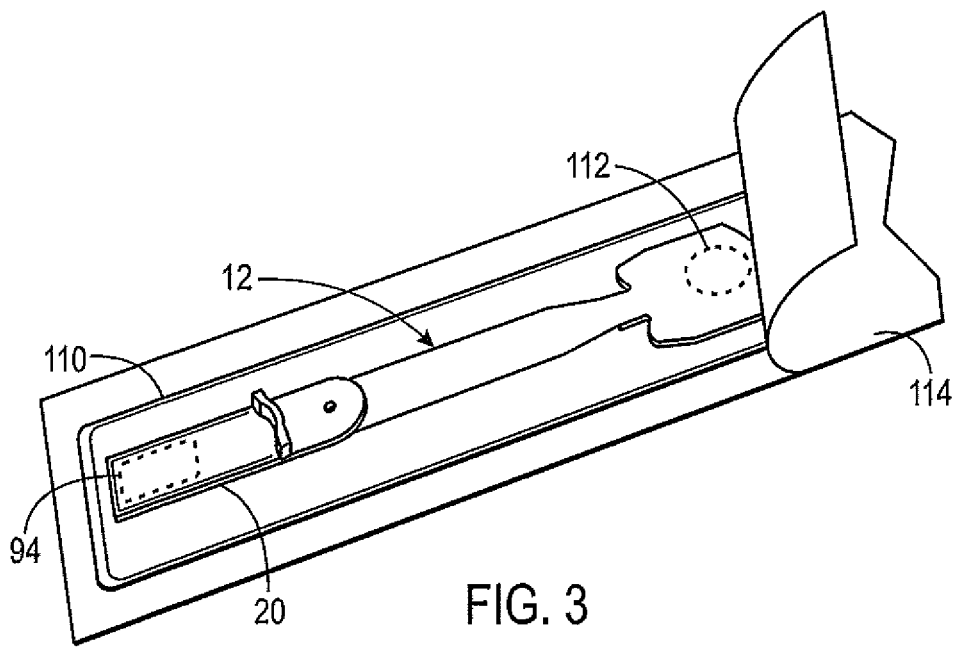
FIG. 3 is a schematic representation of an embodiment of the sensor of FIG. 2 in packaged form, in accordance with an aspect of the present disclosure.

After the sensor 12 is produced, the sensor 12 may be packaged and provided to a medical facility for use. FIG. 3 depicts an embodiment of the manner in which the sensor 12 may be packaged. As illustrated, the sensor 12 is placed on a liner 110, which may include a series of indentations 112 for receiving each of the gel support structures 100. The liner 110 may include any suitable lining material that is appropriate for use in conjunction with the materials of the sensor 12 and the conductive gel 96. As an example, the liner 110 may include a siloxane material, a polyethylene liner material, a polystyrene liner material, a polyester liner material, or the like.

The sensor 12 and liner 110 are contained within a packaging 114. The packaging 114 may include a packaging material suitable for retaining the moisture of the conductive gel 96 when the sensor 12 is stored. That is, the packaging 114 may prevent the conductive gel 96 of the sensor 12 from drying out, which could prevent the sensor 12 from having a suitable level of electrical conductivity with the patient. Accordingly, the packaging 114 will generally have a moisture vapor transmission rate (MVTR) that is sufficiently low to prevent the conductive gel 96 from drying. As an example, the packaging 114 may include metal barrier materials such as an aluminum foil material, polymeric barrier materials such as biaxially oriented polyethylene terephthalate (BoPET), a metalized barrier film (e.g., metalized PET), or any combination thereof.

As noted above, the sensor 12 discussed with respect to FIGS. 1-3 may be manufactured from a combination of new, refurbished, and/or used materials. Indeed, the present embodiments provide various methods for remanufacturing EEG sensors, such as the BIS™ sensors mentioned above, in accordance with the configurations discussed above. For example, FIG. 4 illustrates a generalized sensor remanufacturing method, FIGS. 5-27 illustrate sensor remanufacturing methods for replacing and/or refurbishing various features of the sensor 12, and FIGS. 28-33 each illustrate a connector/memory unit remanufacturing method that can be performed in conjunction with or independently of the methods of FIGS. 5-27.

Figure 4:
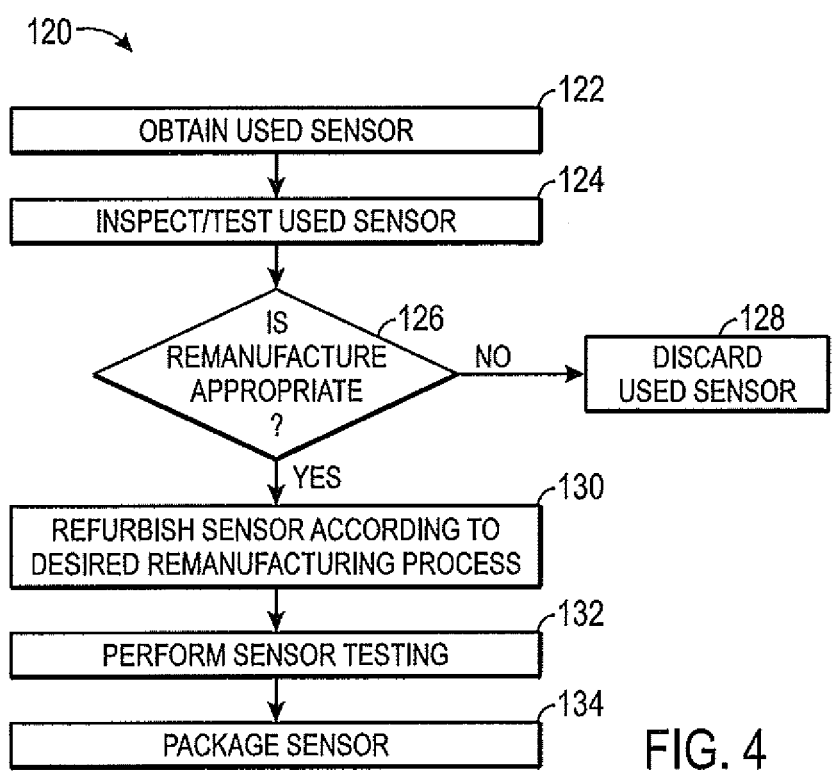
FIG. 4 is a process flow diagram of an embodiment of a general method for remanufacturing the sensor of FIGS. 1-3, in accordance with an aspect of the present disclosure.

Referring now to FIG. 4, an embodiment of a method 120 for remanufacturing a medical sensor (e.g., a BIS™ sensor), such as the sensor 12, is illustrated. The method begins with obtaining a used version of the sensor 12 (block 122). The used version of the sensor 12 may be a single-use medical sensor (i.e., for use on a single patient) or may be a reusable sensor. The sensor 12 may be obtained, as an example, by a technician or similar manufacturing personnel. The sensor 12 may be sterilized before or after the acts represented by block 122 such that the sensor 12 is suitable for handling by a technician or similar worker. The sensor 12 may also undergo inspection and/or testing to determine the operability of the sensor 12 (block 124). As an example, in embodiments where the sensor 12 is a BIS™ sensor, the testing may include testing the operation and accuracy of the electrodes 16, the paddle connector 20, the sensor cable 24, and any other electronic features of the sensor 12, such as the memory unit 94.

After the sensor 12 has been inspected and tested, it may be determined whether it is appropriate to remanufacture the sensor (query 126). For example, it may be determined whether the sensor 12 includes suitable components for remanufacture (e.g., by reviewing the results of the sensor testing acts of block 124 and/or visual inspection). Alternatively or additionally, it may be determined whether the sensor 12 has undergone previous iterations of remanufacturing. Accordingly, the sensor 12 may include one or more indications as to whether the sensor 12 has been previously remanufactured, such an external mark on the sensor 12 or a counter stored on the memory unit 94. For example, the memory unit 94 may track the number of times the sensor 12 has undergone sterilization procedures (e.g., ethylene oxide (EtO) gas, gamma irradiation, autoclaving, chemical sanitation, Pasteurization), memory clearing, memory re-programming, and the like.

In embodiments where remanufacture is not appropriate, the used version of the sensor 12 may be discarded (block 128). For example, one or more features of the used version of the sensor 12 may be inoperative, such as the paddle connector 20, the cable 24, and so on. Depending on the degree to which the sensor 12 may be inoperative, it may no longer be cost-effective to remanufacture, and the sensor 12 may be discarded. In other embodiments, as mentioned above, the sensor 12 may have an external mark or a stored counter that indicates that the sensor 12 is not suitable for remanufacture. Indeed, as discussed herein, the external markings and/or the counter on the memory unit 94 may be incremented with each remanufacturing procedure.

Conversely, in embodiments where it is determined that at least a portion of the sensor 12 is suitable for remanufacturing, the sensor 12 may be remanufactured according to certain remanufacturing processes (block 130). For example, in embodiments where the sensor 12 includes at least some viable components (e.g., the base support layer 60, the electrodes 16 and conductors 84, the paddle connector 20, the memory unit 94), or has one or more indications via the memory unit 94 and/or external marks that remanufacturing is suitable, the sensor 12 may be remanufactured. Embodiments of certain remanufacturing processes are discussed below.

After the sensor 12 has been remanufactured, the sensor 12 is then tested to ensure that it is within certain operational tolerances (block 132). For example, the sensor 12 may be attached or otherwise coupled to a test rig, which may determine and, if suitable, adjust varying operational parameters of the sensor 12. For example, various sensor-specific information may be stored on the memory unit 94, such as conductance-related data if the electrodes 16 and/or conductors 84 are refurbished, information pertaining to the sensor 12 (e.g., the name of the sensor 12, a model code for the sensor 12), or the like. The sensor 12 may then be packaged (block 134) and sent to a medical facility for use.

Figure 5:
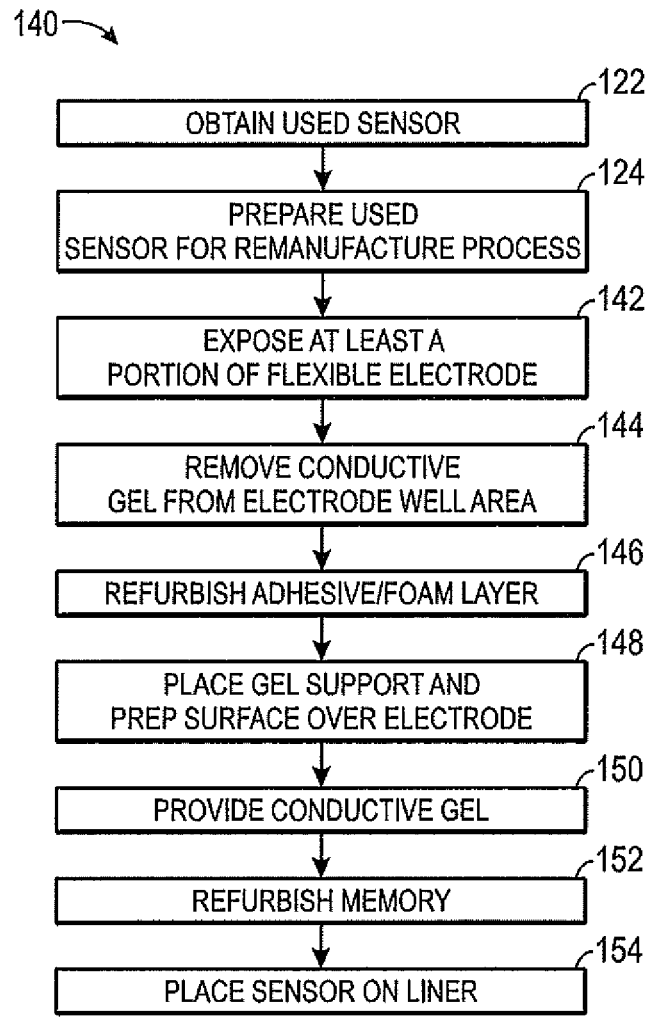
FIG. 5 is a process flow diagram of an embodiment of a method for remanufacturing the sensor of FIGS. 1-3, including refurbishing the body of the sensor, in accordance with an aspect of the present disclosure.

Because portions of the sensor body 18 may contact patient tissue and possibly bodily fluids, it may be desirable, in some situations, to refurbish at least a portion of the sensor body 18 during refurbishment of the sensor 12. Additionally or alternatively, in embodiments where the used version of the sensor 12 includes the memory unit 94, the memory unit 94 may also be refurbished. Accordingly, FIG. 5 illustrates an embodiment of a method 140 for remanufacturing the sensor 12 that includes refurbishing portions of the sensor body 18 and the memory unit 94. The method 130 may include obtaining a used version of the sensor 12 (block 122), which may generally correspond to the acts described above with respect to FIG. 4. That is, the sensor 12 may be obtained directly from a medical facility or from a third party that may obtain the sensor 12 directly or indirectly from a medical facility. Once the sensor 12 is obtained, the sensor 12 may be prepared for remanufacturing (block 124) by sterilization or other preparation steps, as discussed above with respect to FIG. 4.

After the sensor 12 has been prepared for remanufacturing, at least a portion of the electrodes 16 of the sensor 12 may be exposed (block 142). For example, the gel support structures 100, the preparation surfaces 102, the adhesive foam dots 104, or any combination thereof, may be removed from the electrode wells to expose the electrodes 16. In certain embodiments, the gel support structures 100 and the preparation surfaces 102 may be removed from the adhesive foam dots 104 such that only a portion of the electrodes 16 are exposed.

Because the conductive gel 96 may also contact the patient and may not be entirely removed when performing the acts represented by block 142, the conductive gel 96 may be removed from the sensor 12 (block 144). For example, the conductive gel 96 may be removed from the sensor 12 using an aqueous solution (e.g., water, deionized water, or water with a surfactant) to dissolve the conductive gel 96, compressed air to blow the conductive gel 96 out, the conductive gel 96 may simply be wiped out using a cloth or the like, or any combination thereof. In certain embodiments, the conductive gel 96 may be removed using chemical solutions other than aqueous solutions (e.g., organic-based solutions), though it should be noted that it may be desirable to avoid solvents that may undesirably dissolve the base support layer 60 and/or the foam layer 62. Further, in embodiments where a solution is used to remove the conductive gel 96, a drying step may also be performed to remove any remaining liquid from the sensor 12.

Before, during, or after removing the conductive gel 96 from the sensor 12, the foam layer 62 and the adhesive layers 64, 66 may be refurbished (block 146) according to certain protocols, examples of which are described in detail below with respect to FIGS. 13-20. Once the foam layers and adhesive layers 64, 66 have been refurbished, the features that have been removed in accordance with block 142 may be replaced. Embodiments of the manner in which the portion of the support structures 100 are removed in accordance with block 142 and replaced in accordance with block 148 are discussed in further detail below with respect to FIGS. 6-12.

After the gel support structures 100 and the preparation surfaces 102 are in place, the conductive gel 96 is provided (block 150). The acts represented by block 150 may include disposing the conductive gel 96 over the electrodes 16, or providing the conductive gel 96 in a separate dispenser so as to allow a caregiver (e.g., a clinician, nurse, doctor) to dispose the conductive gel 96 in the sensor 12 just before use. In some embodiments, discussed with respect to FIGS. 10 and 11, the conductive gel 96 may have a viscosity sufficient so as to allow the sensor 12 to be used without the gel support structures 100.

The memory unit 94 may also be refurbished (block 152). For example, the memory unit 94 may be cleared, re-programmed, replaced, or the like. Embodiments relating to refurbishing the memory unit 94, such as by replacing or re-programming the memory unit 94, are discussed in further detail below with respect to FIGS. 27-32. Before, during, or after refurbishing the memory unit 94, the sensor 12 may be placed on the liner 110 (block 154). For example, in embodiments where the conductive gel 96 is disposed in the sensor 12, the sensor 12 may be placed on the liner 110 shortly after disposing the conductive gel 96 in the sensor 12 to help retain the conductive gel 96.

Figure 6:
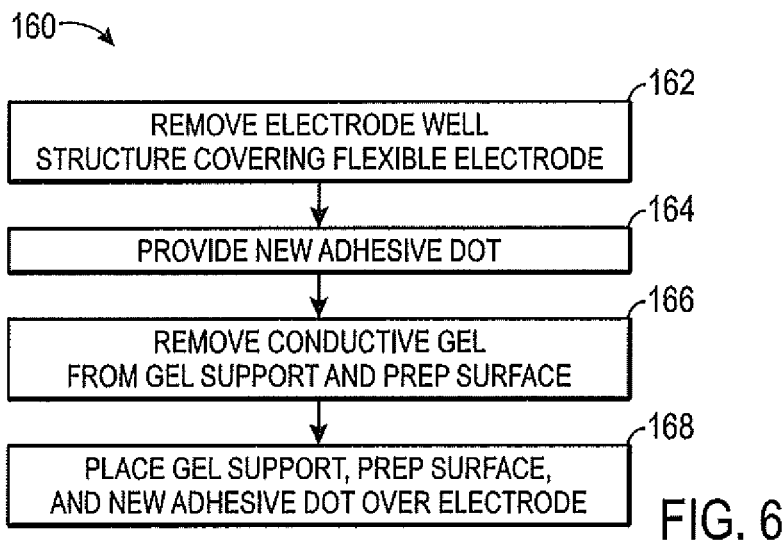
FIG. 6 is a process flow diagram of an embodiment of a method for removing and replacing features disposed within electrode wells of the sensor of FIGS. 1-3, in accordance with an aspect of the present disclosure.

As noted above, the gel support structures 100, the preparation surfaces 102, the adhesive foam dots 104, or any combination thereof, may be removed and/or replaced during remanufacture of the sensor 12. One embodiment of a method 160 for refurbishing the electrode well supporting structures 100 is illustrated in FIG. 6. The method 160 may include removing the preparation surfaces 102 and the adhesive foam dots 104 from the electrodes 16 (block 162). For example, the preparation surfaces 102 may be removed from the adhesive foam dots 104, and the adhesive foam dots 104 may be removed from the sensor 12 by shaving, peeling, or pulling the adhesive foam dots 104 away from the electrodes 16. Because the adhesive foam dot 104 may be damaged or otherwise unsuitable for use in the remanufactured sensor 12, a new adhesive foam dot 104 may be provided (block 164).

In certain situations, the gel support structures 100 and the preparation surfaces 102 may be removed from the sensor 12 before the conductive gel 96 is removed (e.g., in block 144 of FIG. 5). Accordingly, the conductive gel 96 may also be removed from the gel support structures 100 and the preparation surfaces 102 (block 166). For example, as discussed above with respect to block 144 of FIG. 5, the conductive gel 96 may be removed by washing with water, soapy water, another aqueous solution, an organic chemical solution, by wiping, by blowing with compressed air, or any combination thereof. In certain embodiments, because the conductive gel 96 trapped within the electrode well support structures 100 and/or the preparation surfaces 102 may contain debris from a previous use, the either or both may be separately sanitized using EtO gas, autoclaving, Pasteurization, gamma irradiation, or any other suitable sterilization technique known in the art. The gel support structures 100, the preparation surfaces 102, and the new adhesive foam dots 104 may then be disposed on the electrodes 16 (block 168).

Figure 7:
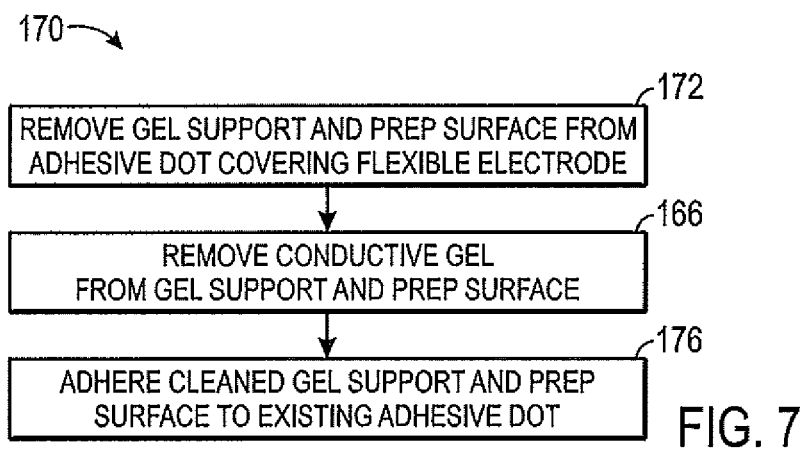
FIG. 7 is a process flow diagram of an embodiment of a method for removing and replacing features disposed within electrode wells of the sensor of FIGS. 1-3, in accordance with an aspect of the present disclosure.

As mentioned above, the adhesive foam dots 104 may be damaged during removal in accordance with block 164 of FIG. 6. Accordingly, it may be desirable to leave the adhesive foam dots 104 within the sensor 12 while removing the gel support structures 100 and the preparation surfaces 102. FIG. 7 illustrates an embodiment of a method 170 in which the used adhesive foam dots 104 are retained within the sensor 12. The method 170 includes removing the gel support structures 100 and the preparation surfaces 102 while leaving the adhesive foam dots 104 attached to the electrodes 16 (block 172). The conductive gel 96 may then be removed from the gel support structures 100 and the preparation surfaces 102 in accordance with block 166 described above. The cleaned gel support structures 100 and the preparation surfaces 102 may then be re-adhered to the adhesive foam dots 104 (block 174).

Figure 8:
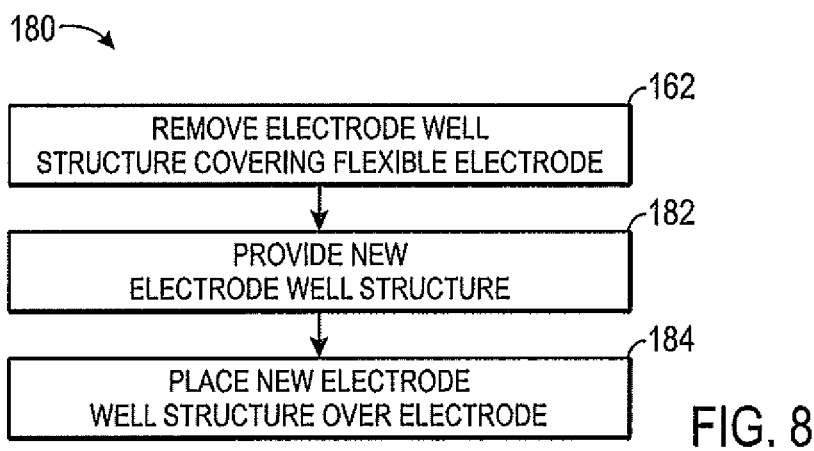
FIG. 8 is a process flow diagram of an embodiment of a method for removing and replacing features disposed within electrode wells of the sensor of FIGS. 1-3, in accordance with an aspect of the present disclosure.

Rather than performing steps to clean the gel support structures 100 and the preparation surfaces 102, it may be desirable to simply replace the gel support structures 100 and the preparation surfaces 102 with new materials. FIG. 8 illustrates an embodiment of one such method 180 for replacing the electrode well structures 106. The method 180 includes removing the electrode well structures 106 from the electrodes 16 (block 162), as discussed above with respect to FIG. 6. New electrode well structures 106 may be provided (block 182). It should be noted that the new electrode well structures 106 may be the same or different than the used versions, depending on cost of replacement or other considerations, such as new or improved materials, or the like. The new electrode well structures 106 may then be adhered to the electrodes 16 (block 184).

Figure 9:
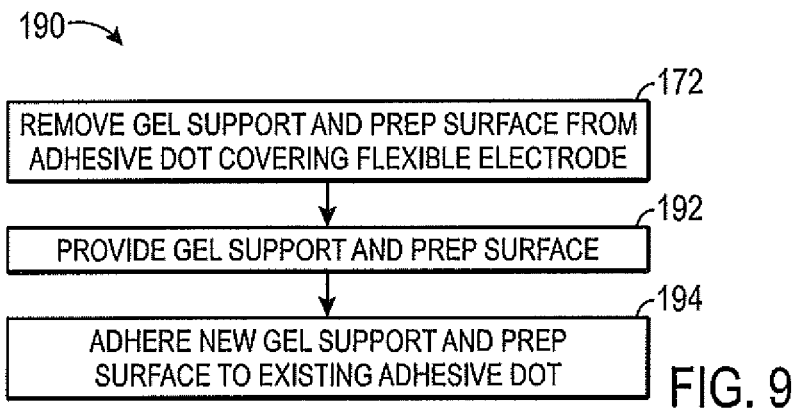
FIG. 9 is a process flow diagram of an embodiment of a method for removing and replacing features disposed within electrode wells of the sensor of FIGS. 1-3, in accordance with an aspect of the present disclosure.

While replacing the entirety of the electrode well structures 106 during remanufacture may be performed as described above, it may be desirable to only replace the gel support structures 100 and the preparation surfaces 102. FIG. 9 illustrates one embodiment of such a method 190. The method 190 includes removing the gel support structures 100 and the preparation surfaces 102 from the adhesive foam dots 104 (block 172) as described above with respect to FIG. 7. New gel support structures 100 and the preparation surfaces 102 may be provided (block 192), which may be the same or different than the used gel support structures 100 and the preparation surfaces 102. The new gel support structures 100 and the preparation surfaces 102 may then be adhered to the adhesive foam dots 104 (block 194).

Figure 10:
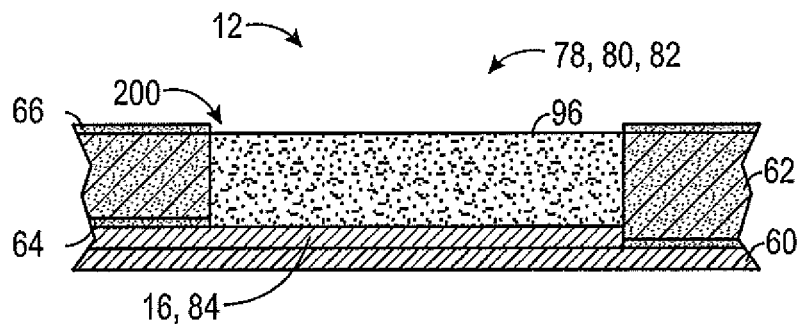
FIG. 10 is a cross-sectional view, taken along line 10-10, of an embodiment of the sensor of FIGS. 1-3 having a self-supporting conductive gel, in accordance with an aspect of the present disclosure.

As noted above, the electrode well structures 106 are generally configured to support the conductive gel 96 within the sensor 12 so as to retain the conductive gel 96 within the sensor 12, and also to prepare the patient for monitoring as the sensor 12 is attached to the patient's forehead and temple (or other somatic region). However, in certain embodiments, the conductive gel 96 may have a sufficient viscosity so as to preclude the use of the gel support structures 100. FIG. 10 is a cross-section of the sensor 12 taken along line 10-10, and illustrates one such embodiment where the conductive gel 96 is self-supporting within an electrode well 200 of the sensor 12. In FIG. 10, the sensor 12 does not include the gel support structures 100. In certain embodiments where the conductive gel 96 is self-supporting, the sensor 12 may include the adhesive foam dot 104 and the preparation surface 102.

Figure 11:
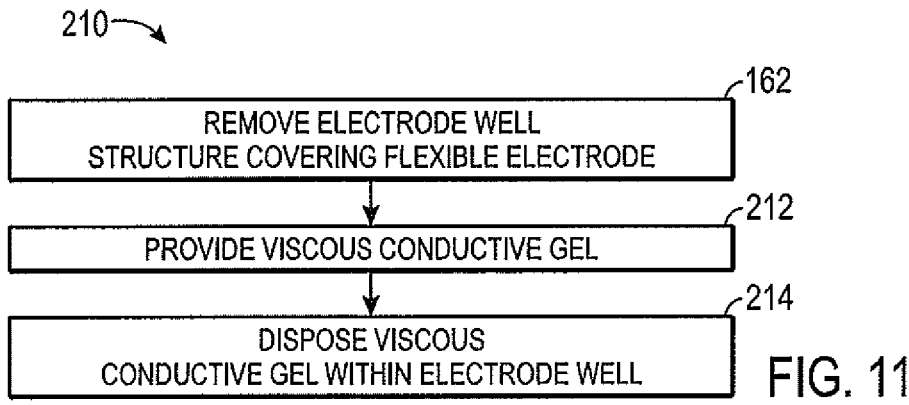
FIG. 11 is a process flow diagram of an embodiment of a method for removing features disposed within electrode wells of the sensor of FIGS. 1-3 and replacing the features with the self-supporting conductive gel of FIG. 10, in accordance with an aspect of the present disclosure.

The cross-section of FIG. 10 also illustrates the self-supporting conductive gel 96 as in direct contact with the electrodes 16, which may be coextensive with the conductors 84. As illustrated, the conductors 84 are disposed underneath the foam layer 62 while the electrodes 16 are exposed. An embodiment of a method 210 for producing the embodiment of the sensor 12 of FIG. 10 from the embodiment of the sensor 12 of FIG. 2 is illustrated in FIG. 11. The method 210 includes removing the electrode well structures 106 from the electrode wells 200 (block 162), as discussed above with respect to FIG. 6. It should be noted that since the electrode well structures 106 are not retained in the remanufactured sensor, they may be discarded or repurposed, for example, for use in another sensor or other medical device. A new conductive gel 96 may be provided (block 212). The new conductive gel 96 may have a viscosity that is the same, or greater than the conductive gel 96 used in the used sensor 12. For example, in embodiments where the new conductive gel 96 is more viscous, the conductive gel 96 may have a higher viscosity by having a lower concentration of water or other fluid, by having a polymer with a greater molecular weight, by having a polymer with a lower solubility, or the like. The viscous conductive gel 96 may then be disposed in the electrode wells 200 (block 214) in place of the electrode well structures 106.

As discussed above with respect to FIG. 5, the foam layer 62 and the adhesive layers 64, 66 may be refurbished before, during, or after refurbishing the electrode wells 200 and the electrode well structures 106 according to the methods described above. FIGS. 12-19 depict embodiments of methods for refurbishing these layers, and the resulting configurations of the sensor 12. Specifically, FIGS. 12, 14, 15, 17, and 18 each illustrate an embodiment of the acts represented by block 146 of FIG. 5.

Figure 12:
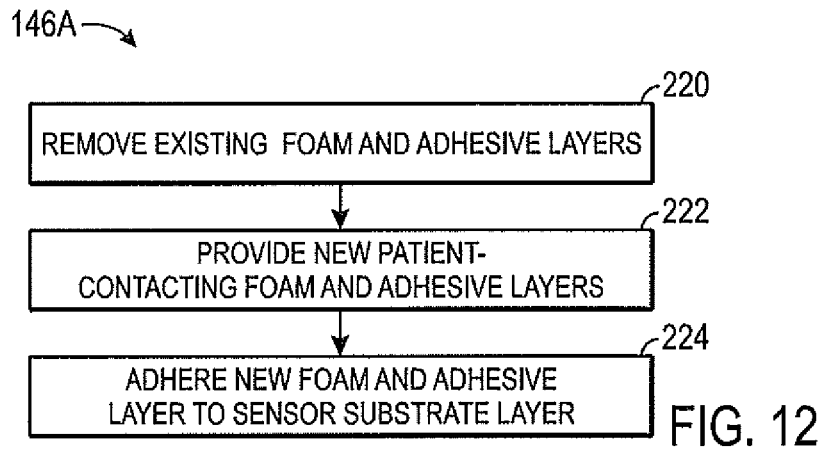
FIG. 12 is a process flow diagram of an embodiment of a method for remanufacturing a body of the sensor of FIGS. 1-3, in accordance with an aspect of the present disclosure.

FIG. 12 illustrates an embodiment of a method 146A that includes replacing the foam layer 62 and adhesives 64, 66. The method 146A may begin by removing the existing foam layer 62 and associated adhesives 64, 66 away from the base structural layer 60 of the sensor 12 (block 220). For example, the sensor 12 may be warmed to reduce the adhesive bond strength of the first adhesive layers 64 to facilitate separation of the foam layer 62 away from the base structural layer 60. In other embodiments, the foam layer 62 and adhesives 64, 66 may be shaved or otherwise cut away from the base structural layer 60. In certain embodiments, the adhesives 64, 66 may be dissolved using a solvent to facilitate removal of the foam layer 62. However, it should be noted that the solvent may be selected so as to dissolve the adhesives 64, 66 without dissolving the foam layer 62 or base structural layer 60. Conversely, in certain embodiments, the foam layer 62 and associated adhesives 64, 66 may be dissolved away from the base structural layer 60.

A new foam layer 62 and adhesives 64, 66 may be provided (block 222). The new foam layer 62 may include the same or different materials compared to the used foam layer 62, and the adhesives 64, 66 may be the same or different than the used adhesives 64, 66. In some embodiments, the new first adhesive 64 disposed between the foam layer 62 and the base structural layer 60 may be selected so as to facilitate removal of the foam layer 62 from the base structural layer 60, for example to facilitate future remanufacturing processes. That is, the new version of the first adhesive 64 may have a lower adhesive bond strength compared to the used version of the first adhesive 64. The material used for the new version of the first adhesive 64 may have a reduced bonding strength compared to the used version. Alternatively or additionally, the new version of the first adhesive 64 may cover a smaller surface area of the foam layer 62 such that the overall bond of the foam layer 62 to the base structural layer 60 is weaker compared to the used version of the sensor 12. The new foam layer 62 and adhesives 64, 66 are then adhered to the base structural layer 60 of the sensor 12 (block 224).

In some embodiments, it may be desirable to retain at least a portion of the used foam layer 62 in the remanufactured sensor 12. For example, in some configurations, the foam layer 62 may be difficult to remove from the base structural layer 60 without damaging the sensor 12. Accordingly, the foam layer 62 may be retained, at least in part. FIG. 13 is a cross-sectional view of an embodiment of the sensor 12 after removing a top portion (i.e., closer to the patient-contacting side) of the foam layer 62 and disposing an additional foam layer 230 over the used foam layer 62. To accommodate the size of the additional foam layer 230, a thickness $t_1$ of the foam layer 62 may be reduced such the sensor 12 may have an optimal overall thickness. The illustrated sensor 12 also includes a new adhesive 232 configured to adhere the additional foam layer 230 to the used foam layer 62, and a patient-contacting adhesive 234 disposed on the additional foam layer 230 configured to adhere the sensor 12 to the patient. The additional foam layer 230 may include the same foam material as the used foam layer 62, may include different foam materials than the used foam layer 62, or a combination. Likewise, the adhesives 232, 234 may be the same or different compared to the adhesives 64, 66.

As noted above with respect to FIG. 2, FIG. 13 also provides a cross-sectional view of the adhesive foam dot 104 disposed between first and second adhesives 236, 238, which may be coated or layered on the adhesive foam dot 104. The first adhesive 236 is configured to adhere the adhesive foam dot 104 to the electrode 16, and the second adhesive 238 is configured to adhere the adhesive foam dot 104 to a plastic backing 240 of the preparation surface 102.

Figure 14:
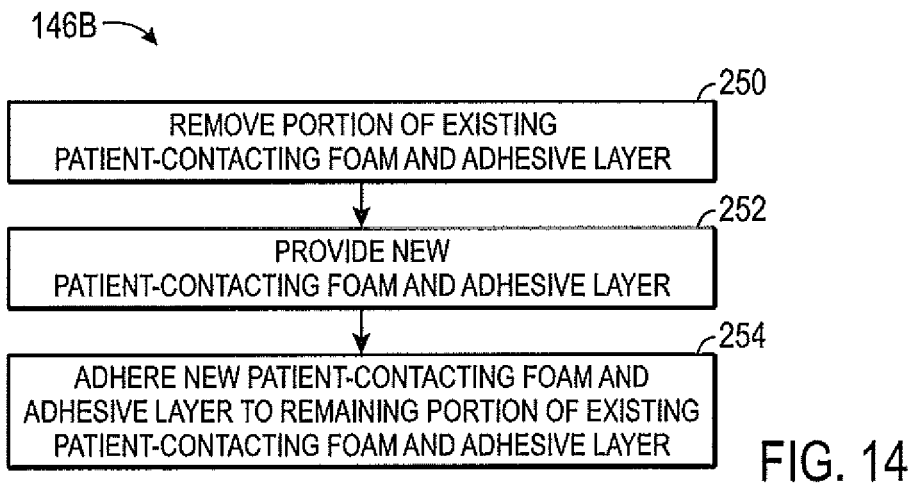
FIG. 14 is a process flow diagram of an embodiment of a method for remanufacturing a body of the sensor of FIGS. 1-3, in accordance with an aspect of the present disclosure.

An embodiment of a method 146B for producing the sensor 12 of FIG. 13 is illustrated in FIG. 14. The method 146B includes removing a portion of the foam layer 62 (block 250), which may involve shaving, peeling, dissolving, etching, or otherwise separating a first portion of the foam layer 62 away from a second portion of the foam layer 62. It will be appreciated that in removing the portion of the foam layer 62 that the patient-contacting adhesive 66 is removed as well. The additional foam layer 230 and the adhesives 232, 234 may be provided (block 252) and adhered to the remaining portion of the used foam layer 62 (block 254).

Figure 15:
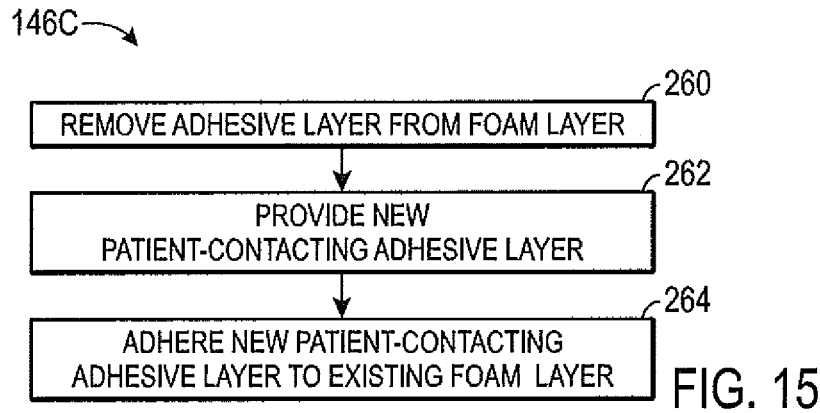
FIG. 15 is a process flow diagram of an embodiment of a method for remanufacturing a body of the sensor of FIGS. 1-3, in accordance with an aspect of the present disclosure.

While the embodiments described above relate to removing the foam layer 62, it may be desirable to retain the foam layer 62 and replace the outermost patient-contacting adhesive 66. FIG. 15 illustrates an embodiment of such a method 146C in which the adhesive 66 is replaced. The method 146C includes removing the patient-contacting adhesive 66 from the foam layer 62 (block 260). For example, in embodiments where the patient-contacting adhesive 66 is a supported adhesive layer, the patient-contacting adhesive 66 may be removed by pulling on the tab 67 such that the patient-contacting adhesive 66 separates from the foam layer 62. In other embodiments, the patient-contacting adhesive 66 may be scraped off, dissolved away, wiped off, or removed by any other suitable adhesive removal technique. A new patient-contacting adhesive 66 may be provided (block 262). The new patient-contacting adhesive 66 may be the same or different adhesive than the used patient-contacting adhesive 66, and may include an acrylic adhesive, a supported transfer tape, an unsupported transfer tape, or other suitable adhesive material. The patient-contacting adhesive 66 may then be adhered to the existing foam layer 62 (block 264).

Figure 16:
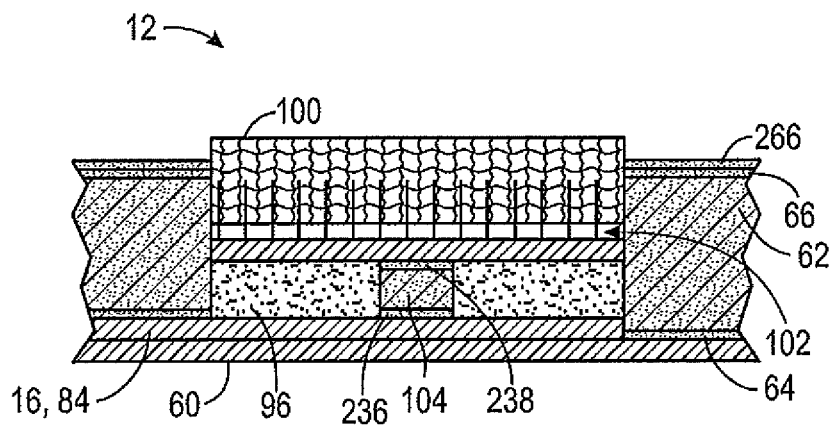
FIG. 16 is a cross-sectional view, taken along line 10-10, of an embodiment of the sensor of FIGS. 1-3 having an additional patient-contacting adhesive disposed over a used patient-contacting adhesive, in accordance with an aspect of the present disclosure.
Figure 17:
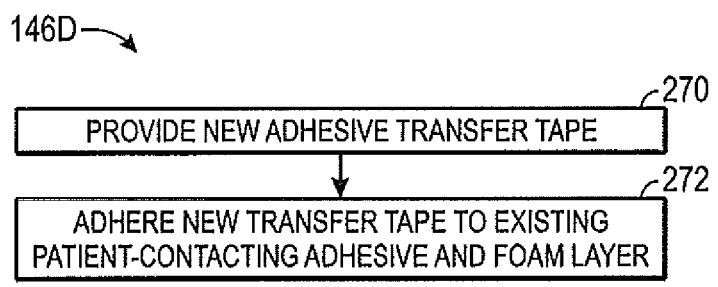
FIG. 17 is a process flow diagram of an embodiment of a method for remanufacturing a body of the sensor of FIGS. 1-3, in accordance with an aspect of the present disclosure.

Rather than removing the used patient-contacting adhesive 66 as discussed above, as illustrated in FIG. 16, it may be desirable to refurbish the sensor 12 by disposing a new patient-contacting adhesive 266 directly over the used patient-contacting adhesive 66. The new patient-contacting adhesive 266 may be the same or different than the used patient-contacting adhesive 66, and may be a supported or unsupported transfer tape, an adhesive coating, or any adhesive capable of attaching the sensor 12 to the patient. An embodiment of a method 146D for producing the sensor 12 of FIG. 16 is illustrated in FIG. 17. The method 146D includes providing the new adhesive 266 (block 270), which may be a supported or an unsupported transfer tape layer, or an adhesive coating, as noted above. The new patient-contacting adhesive 266 may then be adhered to the used patient-contacting adhesive 66 (block 272), which may include laminating the new patient-contacting adhesive 266 on the used patient-contacting adhesive 66 or coating the new patient-contacting adhesive 266 on the used patient-contacting adhesive 66.

Figure 18:
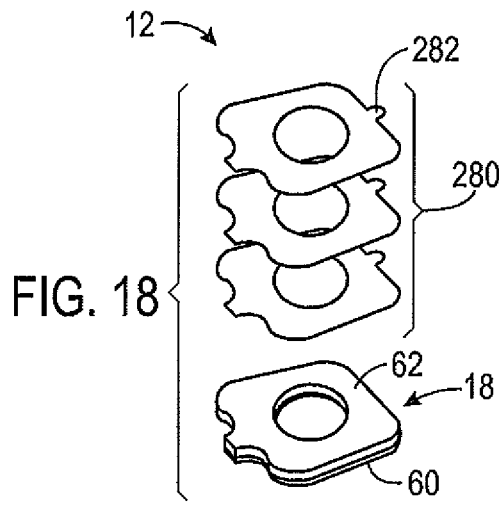
FIG. 18 is an exploded perspective view of an embodiment of the sensor of FIGS. 1-3 and illustrating a plurality of patient-contacting layers laminated over a foam layer of the sensor, in accordance with an aspect of the present disclosure.

To facilitate future remanufacturing of the sensor 12, it may be desirable to provide a plurality of adhesive layers 280 disposed over the foam layer 62, as illustrated in FIG. 18. In FIG. 18, the plurality of adhesive layers 280 are positioned over the first electrode portion 76A of the sensor 12, though it should be noted that FIG. 18 is generally representative of multiple adhesive layers 280 positioned over the entire sensor body 18. In certain embodiments, one adhesive layer 280 may be removed after each patient use. For example, after a patient is monitored using the sensor 12, one of the adhesive layers 280 may be removed (e.g., during remanufacture) to expose a new adhesive layer 280. In some embodiments, the number of adhesive layers 280 may be such that after the adhesive layers 280 are exhausted, the sensor 12 may no longer be suitable for remanufacture. The adhesive layers 280 may also each include a tab 282 to facilitate removal during remanufacture. In other embodiments, the adhesive layers 280 may enable the sensor 12 to be used on a single patient over several uses. The adhesive layers 280 may include any adhesive material suitable for use in medical devices, such as acrylic-based adhesives, transfer tape adhesives, or the like.

Figure 19:
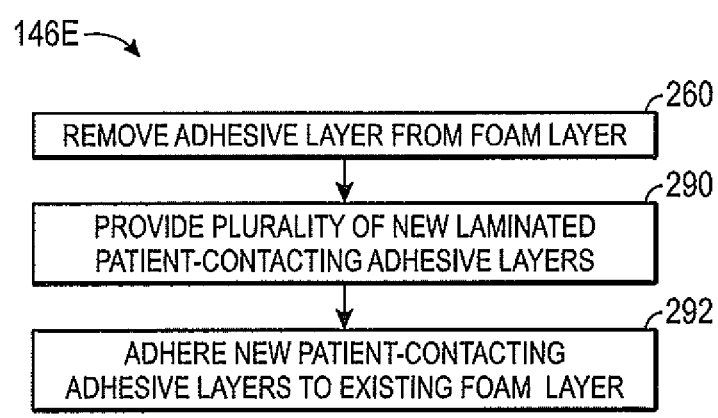
FIG. 19 is a process flow diagram of an embodiment of a method for remanufacturing a body of the sensor of FIGS. 1-3, in accordance with an aspect of the present disclosure.

One embodiment of a method 146E for producing the sensor 12 of FIG. 18 is illustrated in FIG. 19. The method 146E includes removing the used patient-contacting adhesive layer 66 from the foam layer 62 (block 260), as discussed above with respect to FIG. 15. For example, the used patient-contacting adhesive layer 66 may be pulled, shaved, dissolved, or otherwise separated from the foam layer 62. It should be noted, however, that in some embodiments the used patient-contacting adhesive 66 may be retained. The plurality of new adhesive layers 266 may be provided (block 290) and adhered to the existing foam layer 62 of the sensor 12 (block 292).

In addition to or in lieu of remanufacturing portions of the body 18 of the sensor 12 as described above, it may be desirable to remanufacture other portions of the sensor 12, such as the electrodes 16 and/or the conductors 84. In accordance with certain embodiments of the present disclosure, as noted, the electrodes 16 and conductors 84 may include a conductive ink composition having a mixture of a conductive metal and metal ion, such as an Ag/AgCl mixture. Accordingly, refurbishing the electrodes 16 and conductors 84 may include re-printing, re-ionizing, or otherwise replenishing the conductive ink. While the sensor 12 may be refurbished without replenishing the conductive ink, it should be noted that the shelf life of the sensors 12 described herein may be greatly reduced when refurbishment of the electrodes 16 and/or conductors 84 is not performed. For example, the electrodes 16 and conductors 84 may have poor conductivity, a lack of impedance, or similar diminished electrical properties such that the sensor 12 may not be suitable for performing BIS measurements after a certain amount of time. Accordingly, in embodiments where the electrodes 16 and conductors 84 include a conductive ink as described above, it may generally be desirable to replenish the conductive ink during remanufacture of the sensor 12.

Figure 20:
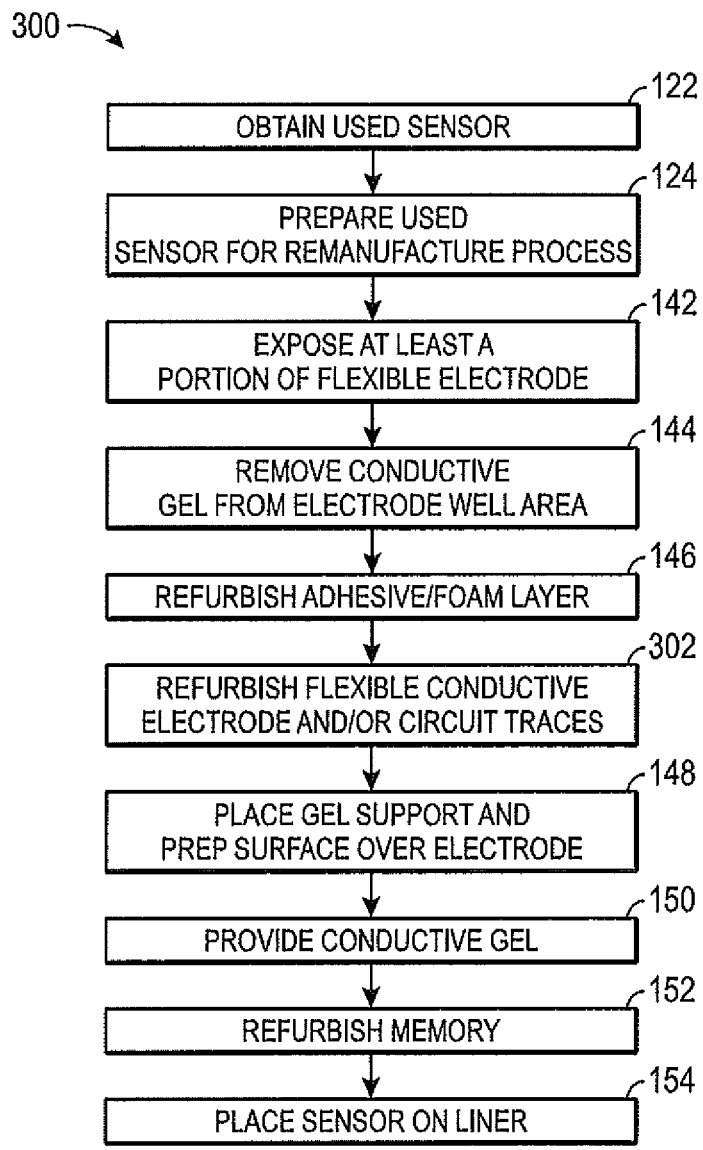
FIG. 20 is a process flow diagram of an embodiment of a method for remanufacturing the sensor of FIGS. 1-3 including replenishing the conductive ink of the electrodes and/or conductors of the sensor, in accordance with an aspect of the present disclosure.

Indeed, an embodiment of a general method 300 for remanufacturing the sensor 12 that includes remanufacturing the electrodes 16 and/or conductors 84 is illustrated in FIG. 20. The method 300 includes several steps that are the same as those described above with respect to FIG. 5. Accordingly, those steps are discussed using the same reference numerals as used in FIG. 5. Indeed, the method 300 includes the same acts represented by blocks 122, 124, 142, 144, 146, 148, 150, 152, and 154 as described above with respect to FIG. 5. Thus, as discussed above, the used version of the sensor 12 may be obtained (block 122), which may include obtaining the sensor 12 directly from a medical facility or from a third party that obtains the medical sensor, as discussed above. The sensor 12 may be prepared for the remanufacturing process (block 124), for example by sterilizing the sensor 12, removing debris from the previously monitored patient, performing testing on the sensor 12, or any combination thereof. At least a portion of the electrodes 16 may be exposed (block 142), for example by removing at least a portion of the electrode well structures 106. The conductive gel 96 may also be removed from the electrode wells 200 (block 144) by wiping, dissolution, blowing, or any combination thereof, as discussed above. The adhesives 64, 66 and the foam layer 62 may also be refurbished (block 146), for example using the methods described above with respect to FIGS. 12, 14, 15, 17, and 19.

The method 300 also includes, as noted, refurbishing the electrodes 16 and/or the conductors 84 (block 302). As discussed in detail below with respect to FIGS. 21-25, the electrodes 16 and/or conductors 84 may be refurbished by re-printing the conductive ink of the electrodes 16 and/or conductors 84, re-ionization of the conductive ink of the electrodes 16 and/or conductors 84 or printing a metallic ink and ionizing the metallic ink to produce the electrodes 16 and/or conductors 84. After the electrodes 16 and/or conductors 84 are refurbished, the conductive gel 96 may be provided (block 150), as discussed above. The memory unit 94 may also be refurbished (block 152), and the sensor 12 may be disposed on the liner 110 (block 154), as discussed above.

Figure 21:
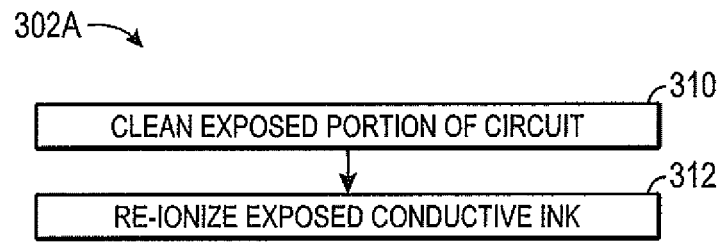
FIG. 21 is a process flow diagram of an embodiment of a method for replenishing the conductive ink of the electrodes and/or conductors of the sensor of FIGS. 1-3, in accordance with an aspect of the present disclosure.
Figure 22:
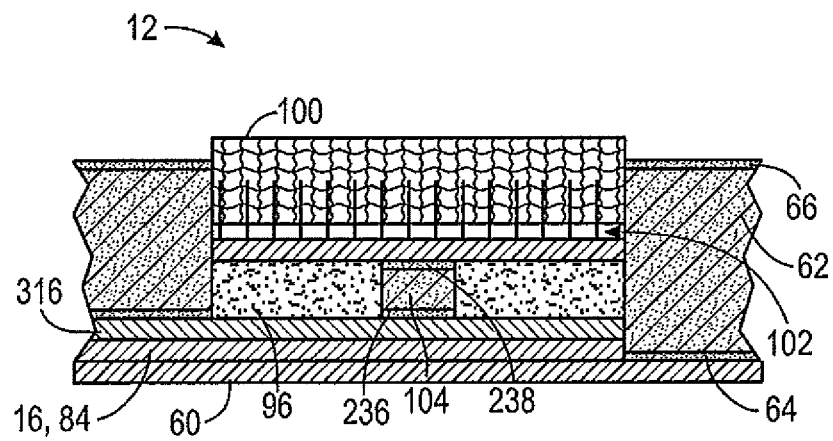
FIG. 22 is a cross-sectional view, taken along line 10-10, of an embodiment of the sensor of FIGS. 1-3 having a new conductive ink disposed over a used conductive ink, in accordance with an aspect of the present disclosure.
Figure 23:
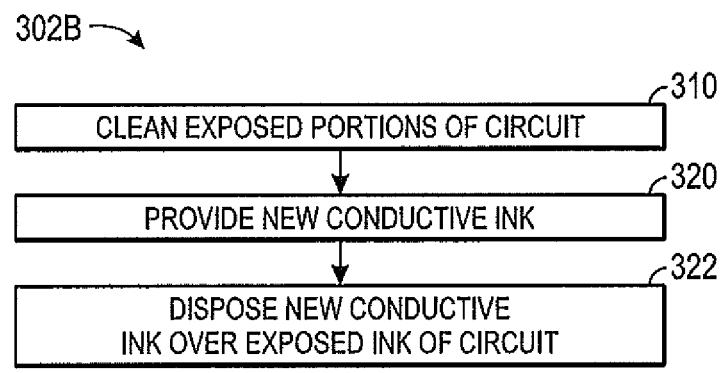
FIG. 23 is a process flow diagram of an embodiment of a method for replenishing the conductive ink of the electrodes and/or conductors of the sensor of FIGS. 1-3, in accordance with an aspect of the present disclosure.

As noted, the electrodes 16 and conductors 84 may include a conductive ink composition that is refurbished according to block 302 of method 300 above. FIGS. 21-23 each illustrate embodiments of methods corresponding to block 302 for replenishing the conductive inks of the electrodes 16 and/or conductors 84. Specifically, FIG. 21 illustrates an embodiment of a method 302A that includes cleaning the portions of the electrodes 16 and/or conductors 84 that are exposed during remanufacture (block 310). For example, in embodiments where the foam layer 62 and adhesives 64, 66 are removed from the sensor 12, the acts represented by block 310 may include ensuring that all adhesive and foam materials are removed from the electrodes 16 and conductors 84. However, in embodiments where only the electrodes 16 are exposed, such as when the foam layer 62 is not removed, the electrodes 16 may be wiped or washed clean, for example to remove any remaining conductive gel 96 and/or remnants of the adhesive foam dots 104.

After the electrodes 16 and/or conductors 84 that are exposed have been suitably cleaned, the conductive ink contained within the exposed portions may be re-ionized (block 312). For example, in embodiments where the conductive ink composition includes a metal chloride salt (e.g., AgCl), the re-ionization step may involve re-chloridating the exposed conductive ink to increase the concentration of metal salt contained within the conductive ink composition. By way of example, the re-chloridation may be performed using half cell potentials. Specifically, in embodiments where the conductive ink is silver-based, the half cell reaction may be used to oxidize the silver to produce silver ions (e.g., Ag to $Ag^+$). It should be noted that while generally any reaction capable of re-ionizing the conductive ink of the electrodes 16 and/or conductors 84 may be performed in accordance with block 312, that, in certain embodiments, a half cell reaction may be desirable to avoid damaging or contaminating other portions of the sensor 12, such as the adhesives 64, 66, the foam layer 62, or the base structural layer 60. For example, half-cell reactions may generally be selective for metallic materials. Therefore, in the present context, a half cell reaction performed in accordance with block 312 may be selective for the used electrodes 16 and/or conductors 84.

In some situations, the conductive ink of the used electrodes 16 and/or conductors 84 may be partially removed or no longer suitable for refurbishment after various remanufacturing steps have been performed. Accordingly, a new conducive ink 316 may be disposed over the used electrodes 16 and/or conductors 84, an embodiment of which is illustrated in FIG. 22. Specifically, FIG. 22 depicts the new conductive ink 316 as disposed directly on top of the used electrodes 16 and/or conductors 84 and in direct electrical contact with the conductive gel 96, and under the adhesive foam dot 104. However, it may be appreciated that in embodiments where the adhesive foam dot 104 is not removed during the remanufacturing process, that the new conductive ink 316 may not be positioned under the adhesive foam dot 104. The new conductive ink 316 may include the same conductive ink composition utilized in the used electrodes 16 and/or conductors 84. Therefore, in one embodiment, the new conductive ink 316 may include a mixture of Ag/AgCl.

Figure 25:
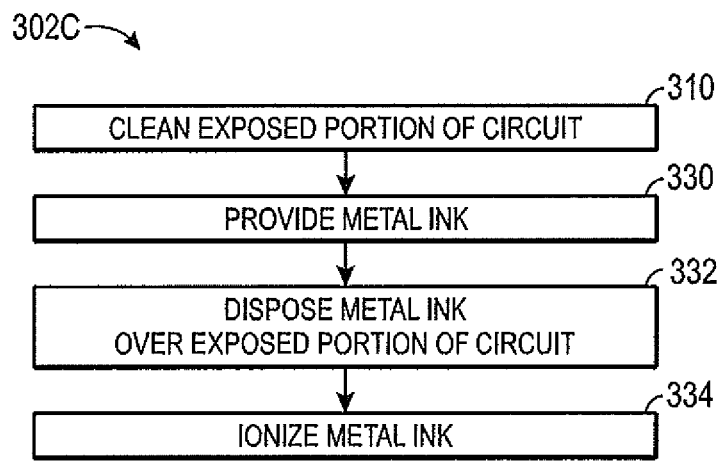
FIG. 25 is a process flow diagram of an embodiment of a method for replenishing the conductive ink of the electrodes and/or conductors of the sensor of FIGS. 1-3, in accordance with an aspect of the present disclosure.
Figure 26:
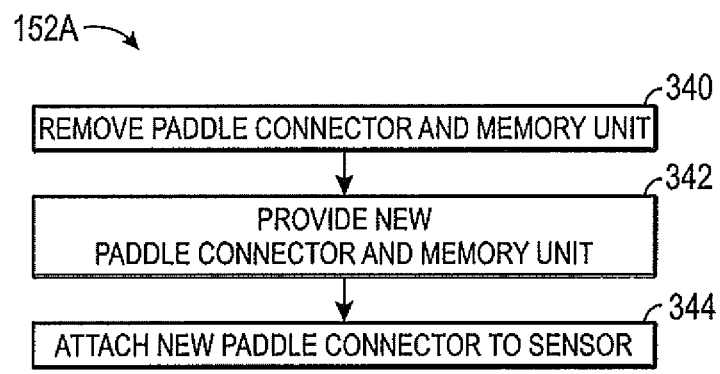
FIG. 26 is a process flow diagram of an embodiment of a method for refurbishing the memory unit of the sensor of FIGS. 1-3, including replacing the connector of the sensor, in accordance with an aspect of the present disclosure.

The embodiment of the sensor 12 illustrated in FIG. 22 may be produced using either of methods 302B of FIG. 23 or 302C of FIG. 25, which involve disposing the new conductive ink 316 over the used electrodes 16 and/or conductors 84. Specifically, method 302B includes cleaning the exposed portions of the used electrodes 16 and/or conductors 84 (block 310), as discussed above with respect to FIG. 21. The new conductive ink 316 may be provided (block 320). For example, the new conductive ink 316 may be provided as a liquid ink mixture pre-loaded into a printing cartridge (e.g., for ink jet printing), in a bottle or other liquid-containing vessel, or as a liquid contained within a plastic enclosure (e.g., an ink dot) that is able to be ruptured to release the new conductive ink 316. The new conductive ink 316 may then be disposed over the exposed portions of the used electrodes 16 and/or conductors 84 (block 322). For example, the new conductive ink 316 may be printed (e.g., flexographically or screen printed), painted, poured, or otherwise positioned and disposed over the used electrodes 16 and/or conductors 84.

Figure 24:
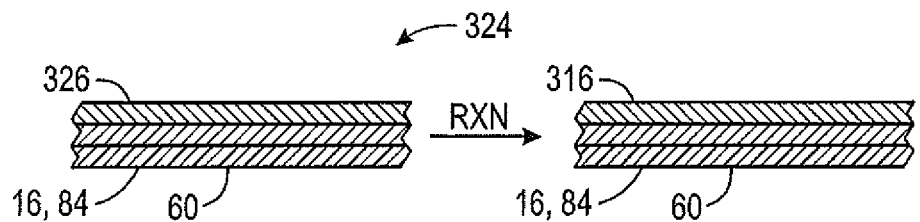
FIG. 24 is a schematic depiction of an embodiment of a process for ionizing a metallic ink disposed on the sensor of FIGS. 1-3, in accordance with an aspect of the present disclosure.

While the new conductive ink 316 may be provided as a pre-made conductive ink composition, it should be noted that in certain embodiments, the new conductive ink 316 may be produced during the remanufacturing process. FIG. 24 schematically depicts an example process 324 for producing the new conductive ink 316 from a metallic ink 326. As illustrated, the metallic ink 326 may be disposed over the used electrodes 16 and/or conductors 84. The metallic ink 326 may include a composition or solution of a metal in its reduced form, such as Ag. A reaction, such as a half-cell reaction, may be performed to produce the new conductive ink 316, which includes an oxidized form of the metal, such as $Ag^+$, which may be used to perform BIS or other electrical measurements on a patient, as discussed above. FIG. 25 illustrates an embodiment of a method 302C, which includes the process 324 of FIG. 24.

The method 302C includes cleaning the exposed portions of the used electrodes 16 and/or conductors 84 (block 310), as discussed above with respect to FIG. 21. The method 302C also includes providing the metallic ink 326 (block 330), which as noted above may include a composition or other solution having at least one metal, such as Ag, Cu, or another metal. The metallic ink 326 may be provided as a solution in a container such as a bottle, dropper, or other storage and dispensing vessel. In certain embodiments, the metallic ink 326 may be provided as a dot, which may include the metallic ink 326 disposed within a plastic enclosure. The dot may be ruptured to release the metallic ink 326. The metallic ink 326 may then be disposed over the exposed portions of the used electrodes 16 and/or conductors 84 (block 332). For example, the metallic ink 316 may be printed (e.g., flexographically or screen printed), painted, poured, or otherwise positioned and disposed over the used electrodes 16 and/or conductors 84. The metallic ink 326 may then be ionized (block 334), for example using a half cell reaction or other metal-oxidizing reaction, to produce the new conductive ink 316. As noted above with respect to FIG. 21, generally any reaction capable of ionizing the metallic ink 326 may be performed in accordance with block 334. However, as noted above, a half cell reaction may be desirable to avoid damaging or contaminating other portions of the sensor 12, such as the adhesives 64, 66, the foam layer 62, or the base structural layer 60.

In addition to, or in lieu of, remanufacturing the sensor body 18, the electrodes 16 and/or the conductors 84 in accordance with the methods described above, the memory unit 94 and the paddle connector 20 may be refurbished according to various embodiments. FIGS. 26, 27, 29, 30, and 31 each illustrate embodiments of methods for refurbishing the memory unit 94 and/or the paddle connector 20 of the sensor 12. Method 152A of FIG. 26 includes removing the paddle connector 20, which includes the memory unit 94, from the sensor 12 (block 340). For example, referring to the embodiment illustrated in FIG. 1, the paddle connector 20 may be removed from the cable 24 (e.g., a patient adapter cable) and the paddle connector 20 may also be removed from the sensor 12.

Once the paddle connector 20 and associated memory unit 94 have been detached from the sensor 12, a new paddle connector 20 having the new memory unit 94 may be provided (block 342). The paddle connector 20 and/or new memory unit 94 may have the same or a similar configuration compared to the used memory unit 94. In some embodiments, the new memory unit 94 may include stored code that enables new or enhanced functionality for the sensor 12 (e.g., when connected to the monitor 14), such as increased patient history functionality and/or updated operational information that reflects any updates, upgrades, or other changes that have been made to the sensor 12. For example, in embodiments where the electrodes 16 and/or conductors 84 are refurbished, new calibration data relating to their conductivity may be written to the memory unit 94. The new paddle connector 20 and memory unit 94 may then be attached to the sensor 12 (block 344).

Figure 27:
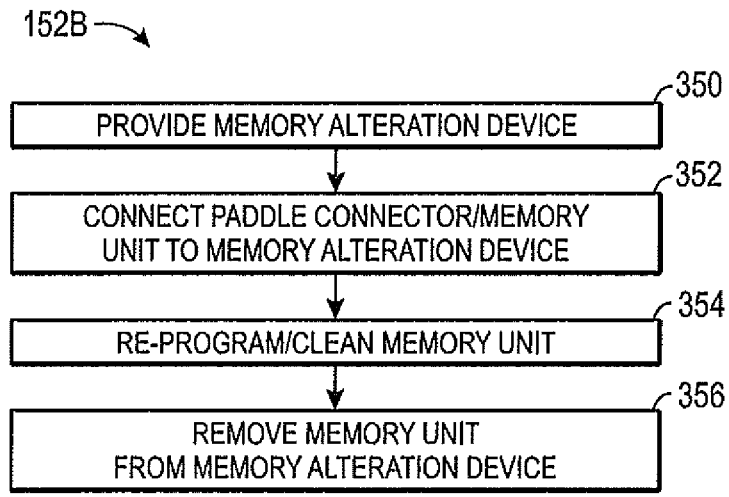
FIG. 27 is a process flow diagram of an embodiment of a method for refurbishing the memory unit of the sensor of FIGS. 1-3, including re-programming the memory unit contained within the connector of the sensor, in accordance with an aspect of the present disclosure.

Because the paddle connector 20 and associated memory unit 94 may represent a signification portion of the overall cost for each sensor 12, it may be desirable to retain the paddle connector 20 and memory unit 94 and simply re-program the memory unit 94. FIG. 27 illustrates an embodiment of a method 152B for re-programming the memory unit 94. The method 152B includes providing a memory alteration device (not shown) (block 350), which may include a computer or other processor-based device that is capable of accessing and deleting at least a portion of the data stored on the memory unit 94. Indeed, the memory alteration device may be an application-specific or a general-purpose computer having code configured to re-program the memory unit 94 contained within the paddle connector 20. Furthermore, the memory alteration device may include one or more ports for coupling to the paddle connector 20 or to the memory unit 94, or both.

After the memory alteration device is provided, the paddle connector 20 and/or memory unit 94 may be coupled to the alteration device (block 352). As noted above, the memory alteration device may include a port that couples to the paddle connector 20 through which the memory alteration device is able to access and re-program the memory unit 94. Alternatively or additionally, the memory alteration device may include a port that specifically receives the memory unit 94, such that the memory unit 94 may be removed from the paddle connector 20 and coupled directly to the memory alteration device for re-programming.

Once the memory unit 94 is directly or indirectly coupled to the memory alteration device, the memory unit 94 may be cleared or otherwise re-programmed (block 354). For example, in embodiments where the memory unit 94 has time-out functionality that causes the sensor to become non-functional after a given number of connections, uses, or after a certain amount of time in operation, the memory alteration device may re-set the number of connections, uses, or time in operation to zero or another lower threshold value. Alternatively or additionally, in embodiments where the memory unit 94 contains stored patient or other historical data, the memory alteration device may clear the historical data. As noted above, in embodiments where the electrodes 16 and/or the conductors 84 are replaced, new or updated calibration data may be written to the memory unit 94. In certain embodiments, sensor-related information may be written to the memory unit 94, which may be displayed on the display of a monitor to which the sensor 12 may attach (e.g., the display 34 of the EEG monitor 14). For example, the memory unit 94 may be programmed such that the type of sensor is displayed (e.g., the name or model number of the sensor). Further, an indication that the sensor 12 has been remanufactured may be provided along with the type of sensor. For example, for a disposable BIS™ Quattro sensor from Aspect Medical Systems, Inc. the display 34 may read "Quattro-R," with "Quattro" indicating the model of the sensor 12 and "-R" indicating that the sensor 12 is a remanufactured sensor.

Figure 28:
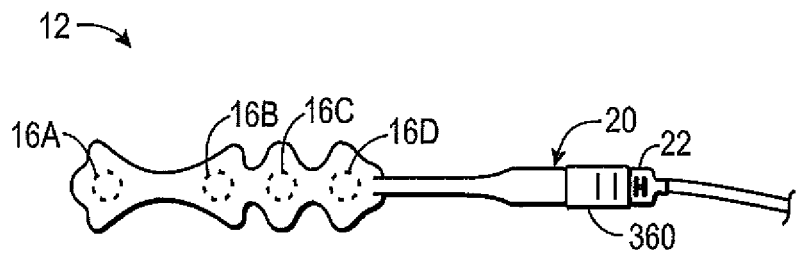
FIG. 28 is a front view of an embodiment of the sensor of FIGS. 1-3 having an adapter coupled to the connector for altering the operability of the memory unit, in accordance with an aspect of the present disclosure.
Figure 29:
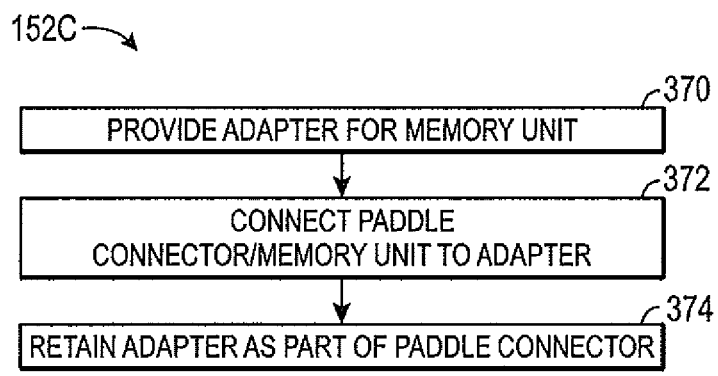
FIG. 29 is a process flow diagram of an embodiment of a method for refurbishing the memory unit of the sensor of FIGS. 1-3, including providing an adaptor for the time-out feature contained within the connector of the sensor, in accordance with an aspect of the present disclosure.

After the memory unit 94 is cleared and/or re-programmed, the memory unit 94 may be removed from the memory alteration device (block 356) and may be suitable for use in conjunction with a remanufactured sensor (i.e., sensor 12). However, rather than re-programming or replacing the memory unit 94 as set forth above, it may be desirable to use an adapter 360, as illustrated in FIG. 28, that is configured to manipulate a data stream to and/or from the memory unit 94 to enable continued operation of the sensor 12, even after a predetermined number of connections, uses, and/or time has been exceeded. As illustrated in FIG. 28, the adapter 360 is coupled directly to the paddle connector 20 and the connector 22 of the cable 24, though the adapter 360 may be configured to couple to a variety of connectors, such as a connector of the EEG monitor 14. The embodiment of the sensor 12 illustrated in FIG. 28 may be produced by a method 152C, which is illustrated in FIG. 29.

The method 152C may include providing the adapter 360 for the memory unit 94 (block 370). Again, the adapter 360 may be configured to manipulate data transmitted to the memory unit 94 such that the memory unit 94 receives data indicative of a reduced number of connections, a reduced operation time, and/or a reduced number of uses. Alternatively or additionally, the adapter may manipulate data transmitted from the memory unit 94 to the EEG monitor 14 such that the memory unit 94 transmits data indicative of a reduced number of connections, a reduced operation time, and/or a reduced number of uses to the EEG monitor 14. The paddle connector 20 may be connected to the adapter 360 (block 372). Due to its mode of operation, as illustrated in FIG. 28, the adapter 360 may be retained as a part of, or integral with, the paddle connector 20 (block 374).

Figure 30:
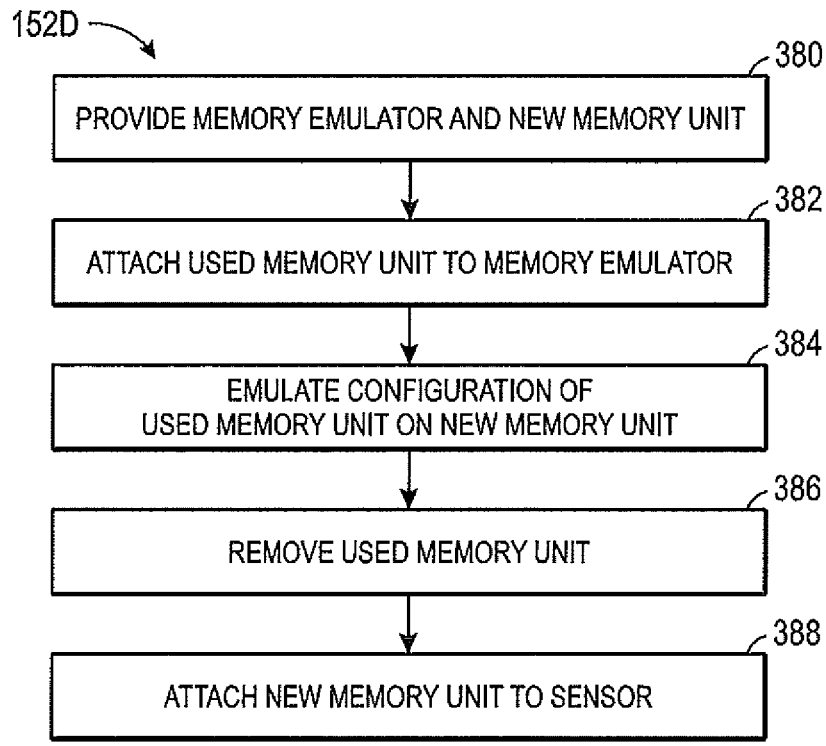
FIG. 30 is a process flow diagram of an embodiment of a method for refurbishing memory unit of the sensor of FIGS. 1-3, including emulating the memory unit on a new memory unit, in accordance with an aspect of the present disclosure.

In situations where the original memory unit 94 components and/or the original programming for the memory unit 94 are not available, it may be desirable to emulate the original memory unit 94. For example, it may be desirable to emulate the original memory unit 94 using a replacement memory unit 94 that has been programmed to mimic the function of the original memory unit. FIG. 30 illustrates an embodiment of such a method 152D, which may be performed in conjunction with certain of the sensor remanufacturing methods described above, or may be performed independently.

The method 152D includes providing a memory emulator (not shown) and a replacement memory unit 94 (block 380). For example, a memory emulator may include an application-specific or general purpose processor-based device (e.g., a computer) that is configured to interface with the original memory unit 94 and/or the paddle connector 20 that includes the memory unit 94. The new memory unit 94 may include a memory device that is capable of being programmed in a similar manner to the original memory unit 94, such as an erasable programmable read-only memory (EPROM). The replacement or new memory unit 94 may also interface with the memory emulator such that the new memory unit 94 may be suitably programmed by the memory emulator to mimic the output of the original memory unit 94. The used memory unit 94, or the used paddle connector 20 having the memory unit 94, may then be attached to the memory emulator (block 382). For example, the memory emulator may include a memory interface, such that the used memory unit 94 is removed from the paddle connector 20 before coupling to the memory emulator. In other embodiments, the paddle connector 20 may directly connect to the memory emulator.

Once the used memory unit 94 is directly or indirectly connected to the memory emulator, the memory emulator may attempt to automatically, or in conjunction with a technician, emulate the operation of the used memory unit 94. For example, the output of the used memory unit 94 may be analyzed, and the memory emulator may attempt to mimic or otherwise simulate the output of the used memory unit 94. Once the memory emulator has produced one or more routines that are able to suitably match the output of the used memory unit 94, the new memory unit 94 may be programmed to emulate the configuration of the used memory unit 94 (block 384).

After the operation of the used memory unit 94 is suitably emulated, the used memory unit 94 may be removed from the used/remanufactured sensor 12 (block 386). For example, the used memory unit 94 may be removed from the paddle connector 20, or the paddle connector 20 may be removed from the sensor 12. In embodiments where the memory unit 94 has already been removed from the paddle connector 20 during the emulation process, the paddle connector 20 may be removed from the sensor 12. Indeed, once the used memory unit 94 has been removed, the new memory unit 94, which emulates the operation of the used memory unit 94, may be attached to the sensor 12 (block 388). For example, in embodiments where the used memory unit 94 has been removed from the paddle connector 20, the new memory unit 94 may be integrated into the paddle connector 20. However, in embodiments where the used paddle connector 20 has been removed, a new paddle connector 20 may be provided that includes the new memory unit 94.

Figure 31:
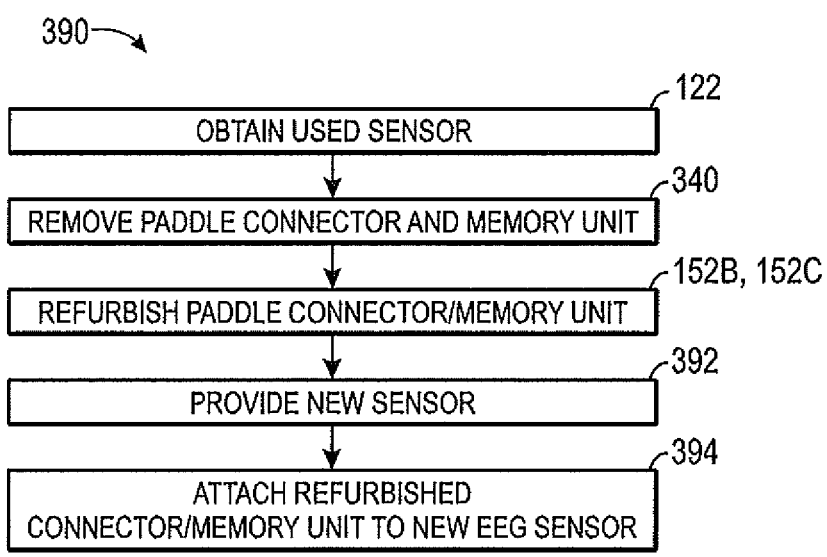
FIG. 31 is a process flow diagram of an embodiment of a method for remanufacturing the sensor of FIGS. 1-3 including retaining only the connector and memory unit and replacing the used sensor with a new sensor, in accordance with an aspect of the present disclosure.

Again, the paddle connector 20 and memory unit 94 may represent a considerable amount of the total cost of the sensors described herein. Indeed, while it may be cost-effective to remanufacture various portions of the sensor 12 including the sensor body 18, the electrodes 16 and conductors 84, it may be desirable to incorporate the used memory unit 94 and, in some embodiments, the paddle connector 20, into a new sensor, such as the sensor 12 or another type of sensor. With this in mind, FIG. 31 illustrates an embodiment of a method 390 for integrating a used paddle connector 20 and associated memory unit 94 with a new sensor.

Method 390 includes obtaining the used version of the sensor 12 (block 122) as described above with respect to FIGS. 4 and 5. For example, the sensor 12 may be obtained after the sensing and memory components have been tested (e.g., from a testing facility), after the sensor 12 has been sterilized (e.g., from a sterilization facility), or after the sensor 12 has been used to monitor a patient (e.g., from a medical facility). The paddle connector 20 and memory unit 94 may then be removed (block 340) as described above with respect to FIG. 26. For example, the paddle connector 20 having the memory unit 94 may be removed from the tail portion 86 of the sensor 12.

Before or after removal of the paddle connector 20 from the sensor 12, the memory unit 94 may be remanufactured according to either of methods 152B or 152C described above. A new sensor may also be provided (block 392), such as a sensor having new electrodes 16 and conductors 84, support layers, padding layers, and so forth. It may be appreciated that in embodiments where the memory unit 94 is remanufactured after being removed from the paddle connector 20, that the new sensor may also include a new paddle connector 20 or another type of connector (e.g., a socket-based connector). The remanufactured memory unit 94, or remanufactured memory unit 94 and paddle connector 20 (or other connector), may then be attached to the new sensor (block 394).

Figure 32:
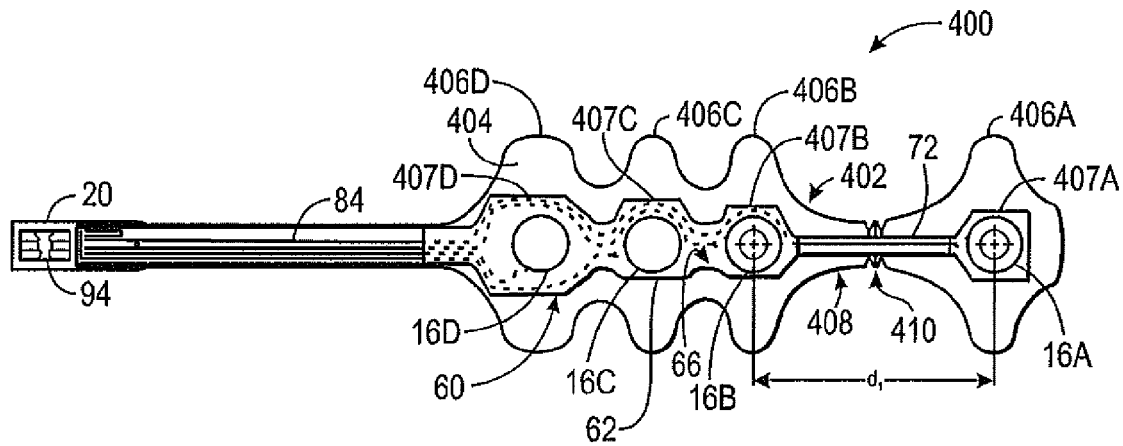
FIG. 32 is a front view of an embodiment of a sensor having new components and remanufactured components from the sensor of FIGS. 1-3, in accordance with an aspect of the present disclosure.

Rather than producing a sensor of the same type or configuration as the sensor 12 of FIG. 2 using the remanufacturing embodiments described herein, it may be desirable to integrate one or more remanufactured components of the sensor 12 into a different sensor design. FIG. 32 illustrates an embodiment of a modified sensor 400, which includes various remanufactured components of the sensor 12 of FIG. 2. Indeed, the modified sensor 400 may have the same or a similar configuration as the sensors described in U.S. patent application Ser. No. 13/074,127 entitled "Method and System for Positioning a Sensor," filed Mar. 28, 2011, which is incorporated by reference herein in its entirety.

Specifically, the modified sensor 400 may include a base material 402, which may be configured to serve as a supporting structure for the remanufactured components of the sensor 12. The remanufactured components may include components which have undergone any of the remanufacturing methods described above, such as the base structural layer 60, the electrodes 16, the conductors 84, the memory unit 94 and paddle connector 20, the foam layer 62, or any combination thereof. The base structural layer 400 may include rubber or elastomeric compositions (including acrylic elastomers, polyimide, silicones, silicone rubber, celluloid, PMDS elastomer, polyurethane, polypropylene, acrylics, nitrile, PVC films, acetates, and latex) to facilitate stretching and conformance to the patient, while the base structural layer 60 of the used sensor 12 may include non-elastomeric, flexible materials such as select polyethylene, polyester or polypropylene plastics. Indeed, it may be desirable to integrate the components of the used sensor 12 into the base material 402 of the modified sensor 400 to provide enhanced conformance and attachment to the patient. Indeed, the modified sensor 400 may include an adhesive 404 disposed on the base material 402 to enable the base material 402 to also secure to the patient.

The modified sensor 400 may include, in a similar manner to the used sensor 12, a plurality of electrode portions 406A-406D, which may each have a different or the same shape as the electrode portions 76 of the sensor 12 illustrated in FIG. 2. In the embodiment illustrated in FIG. 32, however, the plurality of electrode portions 406A-406D may be shaped such that the electrode portions 76 are modified to form new electrode portions 407A-D. The modified sensor 400 may also include a stretchable bridge 408 connecting the electrode portion 406A with the electrode portion 406B. The stretchable bridge 408 may surround the bridge 72, and may be configured enable a varied distance $d_1$ between the electrodes 16A and 16B. The stretchable bridge 408 may have an elasticity that is greater than the bridge 72. Accordingly, the bridge 72 may be folded to accommodate the variance in $d_1$. The stretchable bridge 408 may also include notches 410 that enable rotational movement to allow the electrode 16A to be correctly positioned.

Figure 33:
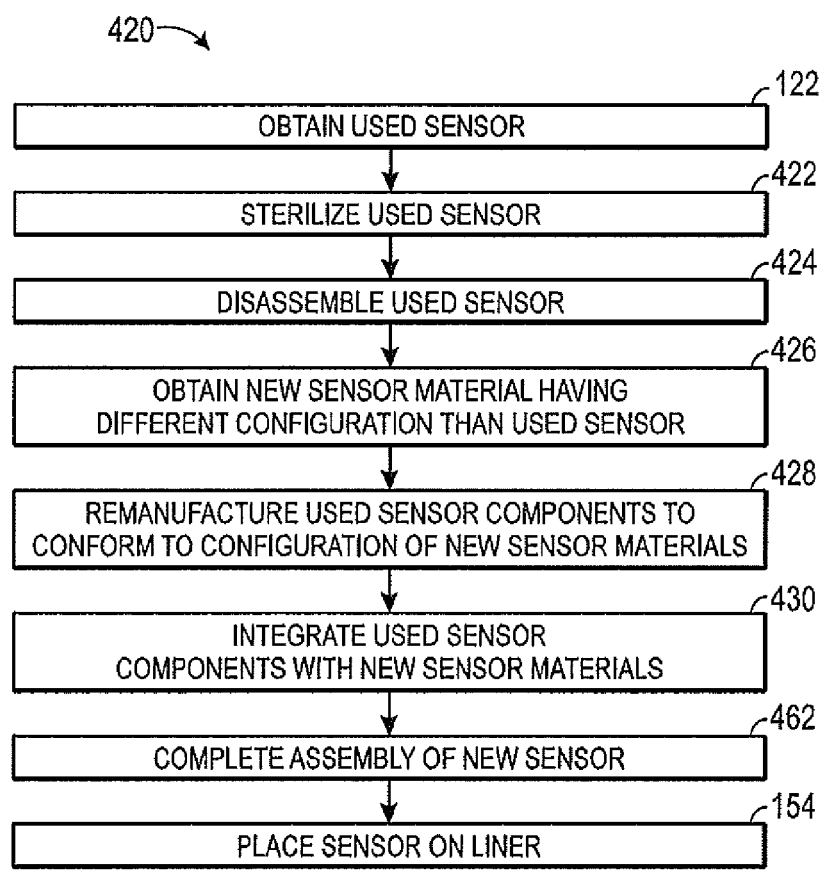
FIG. 33 is a process flow diagram of an embodiment of a method for remanufacturing the sensor of FIGS. 1-3 to produce the sensor of FIG. 32, in accordance with an aspect of the present disclosure.

A method 420 for producing the modified sensor 400 of FIG. 32 is illustrated in FIG. 33. The method 420 includes obtaining the used sensor 12 (block 122), as discussed above with respect to FIGS. 4 and 5. The used sensor 12 may be sterilized (block 422), for example using EtO gas, Pasteurization, autoclaving, disinfecting solutions, gamma irradiation, or the like. The used sensor 12 may then be disassembled (block 424), for example by separating the components of the sensor 12 in the manner illustrated in FIG. 2. However, certain components may be kept coupled together. For example, the base structural layer 60 may remain coupled to the paddle connector 20 and the foam layer 62. Other components, such as the foam the patient-contacting adhesives 66 and/or the electrode well supporting structures 100, may be removed. The patient-contacting adhesive 66 may be replaced to enable the portion of the modified sensor 400 proximate the foam layer 62 to be secured to the patient.

Materials used to produce the modified sensor 400 may be obtained (block 426). For example, the base material 402, additional foam materials, conductive gel 96, and the like, may be obtained. The configuration of the modified sensor 400 may be reviewed, and the used components of the sensor 12 may be remanufactured (block 428). For example, the base structural layer 60 may be re-sized to fit within the base material 402. As illustrated in FIG. 32, the electrode portions 76 of the sensor 12, illustrated in FIG. 2, may be cut so as to form electrode portions 407A-D, which are configured to conform to the shape and size of the electrode portions 406 of the modified sensor 400. Further, the memory unit 94 may be refurbished according to any of methods 152A-D discussed above, and the electrodes 16 and/or conductors 84 may be replenished according to any of methods 302A-C discussed above.

After refurbishment of the desired components of the used sensor 12, the refurbished components may be integrated with the new materials of the modified sensor 400 (block 430). For example, the base structural layer 60 of the used sensor 12 may be disposed on or within, or adhered to the base material 402. Further, new foam or another padding material may be integrated with the base structural layer to provide padding and comfort to the patient. The conductive gel 96 may also be provided as a part of the modified sensor 400, or may be provided in a dispenser for use when the modified sensor 400 is used for patient monitoring.

Once the remanufactured components have been integrated with the new sensor materials of the modified sensor 400, final assembly steps may be performed to complete the modified sensor 400 assembly process (block 462). For example, various adhesives, markings, or the like may be disposed on the base material 402 such that the modified sensor 400 is ready for patient monitoring. The modified sensor 400 may then be placed on the liner 110 (block 154) for future testing, packaging, and delivery to a medical facility.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A remanufactured bispectral index (BIS) sensor, comprising:
   a backing layer;
   first, second, and third electrodes disposed on the backing layer and comprising a conductive ink, wherein the first, second, and third electrodes are adapted to be in electrical contact with a patient to perform BIS measurements;
   a first foam layer disposed on at least a portion of the backing layer;
   a second foam layer disposed on at least a portion of the first foam layer;
   a first adhesive layer configured to secure the first foam layer to the second foam layer; and
   a second adhesive layer attached to the second foam layer and configured to secure the remanufactured BIS sensor to the patient; and wherein at least a portion of one of the first, second, and third electrodes and at least a portion of the backing layer are from a used medical sensor, and the second adhesive layer is new.

2. The remanufactured BIS sensor of claim 1, wherein the conductive ink of the first, second, and third electrodes comprises a silver/silver chloride ink printed on the backing layer, and wherein the first, second, and third electrodes are positioned between the backing layer and the first foam layer.

3. The remanufactured BIS sensor of claim 1, comprising a plurality of conductors printed in the conductive ink on the backing layer, wherein the conductors connect the first, second, and third electrodes to a tail region of the backing layer, and the tail region is configured to attach to a connector.

4. The remanufactured medical sensor of claim 3, comprising the connector, wherein the connector comprises a memory unit storing information relating to the remanufactured BIS sensor that enables a BIS monitor to use the BIS sensor to perform BIS measurements on the patient using at least the first, second, and third electrodes as a ground electrode, a reference electrode, and a signal electrode, respectively.

5. The remanufactured BIS sensor of claim 4, wherein the memory unit is from the used medical sensor and has been re-programmed to enable continued operation of the remanufactured BIS sensor.

6. The remanufactured BIS sensor of claim 4, wherein the memory unit comprises a replacement memory unit configured to emulate an original memory unit of the used medical sensor by simulating an output of the original memory unit based on an analysis of the output of the original memory unit.

7. The remanufactured BIS sensor of claim 4, wherein the memory unit comprises code configured to cause the remanufactured BIS sensor to become non-functional after a predetermined number of uses or after a predetermined period of time.

8. The remanufactured BIS sensor of claim 4, comprising an adaptor coupled to the connector, wherein the adaptor is configured to manipulate data transmitted to or from the memory unit to enable continued operation of the remanufactured BIS sensor.

9. The remanufactured BIS sensor of claim 8, wherein the adaptor is configured to manipulate data transmitted to the memory unit such that the memory unit receives data indicative of a reduced number of connections, a reduced operation time, a reduced number of uses, or a combination thereof.

10. The remanufactured BIS sensor of claim 1, wherein the first and second foam layers each comprise first, second, and third openings corresponding to the respective positions of the first, second, and third electrodes, and the first, second, and third openings and the backing layer form first, second, and third electrode wells.

11. The remanufactured BIS sensor of claim 10, wherein each of the first, second, and third electrodes are coupled to a respective preparation surface configured to prepare the skin of the patient for monitoring.

12. The remanufactured BIS sensor of claim 11, wherein each of the preparation surfaces are coupled to a gel support structure holding a conductive gel, the conductive gel is configured to enable electrical contact between the patient and the first, second, and third electrodes, and wherein the preparation surfaces, the gel support structures, and the conductive gel are new.

13. The remanufactured BIS sensor of claim 1, comprising a fourth electrode comprising the conductive ink disposed on the backing layer, wherein the fourth electrode is adapted to enable the remanufactured BIS sensor to monitor motion artifacts resulting from eye movement.

14. The remanufactured BIS sensor of claim 1, wherein the first foam layer is a remnant foam layer from the used medical sensor.

15. A remanufactured bispectral index (BIS) sensor, comprising:
  a BIS sensor, comprising:
    a backing layer, wherein the backing layer is non-elastomeric; and
    first, second, and third electrodes disposed on the backing layer and comprising a conductive ink, wherein the first, second, and third electrodes are configured to be in electrical contact with a patient to perform BIS measurements; and
    a foam layer disposed on at least a portion of the backing layer;
  a new base layer disposed on the backing layer on a side that is opposite from a side on which the first, second, and third electrodes are disposed, wherein the new base layer is elastomeric; and
  an adhesive attached to the new base layer and configured to secure the remanufactured BIS sensor to the patient;
  wherein the backing layer has a periphery trimmed to fit within a periphery of the new base layer, wherein the backing layer comprises a first backing portion on which the first electrode is disposed, a second backing portion on which the second electrode is disposed, and a first bridge coupling the first and second backing portions, wherein the new base layer comprises a first base portion disposed on the first backing portion, and a second base portion disposed on the second backing portion, and a second bridge coupling the first and second base portions, wherein the second bridge is stretchable to enable a distance between the first and second electrodes to vary and the first bridge is folded to enable the distance between the first and second electrodes to vary, and wherein the second bridge comprises one or more notches to enable rotational movement of the first electrode with respect to the second electrode.

16. The remanufactured BIS sensor of claim 15, wherein the new base layer is a different shape than the backing layer.

* * * * *